US008425864B2

(12) United States Patent
Haywood et al.

(10) Patent No.: US 8,425,864 B2
(45) Date of Patent: *Apr. 23, 2013

(54) APPARATUS FOR TRANSPORTING BIOLOGICAL SAMPLES

(75) Inventors: Bruce C. Haywood, Franklin Lakes, NJ (US); Jamieson William Maclean Crawford, New York, NY (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/295,230

(22) Filed: Nov. 14, 2011

(65) Prior Publication Data

US 2012/0058553 A1    Mar. 8, 2012

Related U.S. Application Data

(60) Division of application No. 11/534,880, filed on Sep. 25, 2006, now Pat. No. 8,071,058, which is a continuation of application No. 10/269,094, filed on Oct. 11, 2002, now Pat. No. 7,147, 826.

(60) Provisional application No. 60/328,407, filed on Oct. 12, 2001.

(51) Int. Cl.
   *B01L 3/00*    (2006.01)
(52) U.S. Cl.
   USPC ......... 422/559; 422/547; 422/549; 422/550; 435/288.1; 435/288.2; 220/23.83; 220/23.87; 220/23.89

(58) Field of Classification Search ............ 422/58, 422/547, 549, 550, 559; 435/283.1, 288.1, 435/288.2; 220/23.83, 23.87, 23.89, 23.9; 206/5.1

See application file for complete search history.

(56) References Cited

U.S. PATENT DOCUMENTS

| 2,302,698 | A | * | 11/1942 | Kessel | 422/552 |
|---|---|---|---|---|---|
| 3,460,552 | A | * | 8/1969 | Sturgeon | 134/135 |
| 4,009,777 | A | | 3/1977 | Thomas | |
| 4,205,747 | A | | 6/1980 | Gilliam et al. | |
| 4,220,252 | A | | 9/1980 | Beall et al. | |
| 4,257,521 | A | | 3/1981 | Poler | |
| 4,277,172 | A | | 7/1981 | Richards | |
| 4,326,306 | A | | 4/1982 | Poler | |
| 4,423,809 | A | | 1/1984 | Mazzocco | |
| 4,439,319 | A | | 3/1984 | Rock | |
| 4,697,697 | A | | 10/1987 | Graham et al. | |
| 4,700,729 | A | * | 10/1987 | Thaler | 134/139 |

(Continued)

*Primary Examiner* — Jill Warden
*Assistant Examiner* — Dwayne K Handy
(74) *Attorney, Agent, or Firm* — The Webb Law Firm

(57) ABSTRACT

A container assembly for storing, treating, transporting and stabilizing a biological sample includes a container, a cap and a sample holder removably received in the container. The sample holder can be a platform-like device dimensioned to be supported on a ledge formed in the side wall of the container. The sample holder includes a central cavity for receiving the sample and immersing the sample in the stabilizing agent in the container. In another embodiment, the sample holder has a closure member for closing the open top end of the cavity. The container includes a liquid reagent in an amount sufficient to treat the biological sample. The biological sample is retained in a predetermined containment area of the container to maintain the biological sample immersed in the reagent without regard to the orientation of the container.

9 Claims, 16 Drawing Sheets

U.S. PATENT DOCUMENTS

| | | |
|---|---|---|
| 4,721,124 A | 1/1988 | Tuerkheimer et al. |
| 4,750,610 A * | 6/1988 | Ryder ............... 206/5.1 |
| 4,801,553 A | 1/1989 | Owen et al. |
| 4,838,413 A * | 6/1989 | Monestere ............... 206/5.1 |
| 4,844,242 A | 7/1989 | Chen et al. |
| 5,019,084 A | 5/1991 | Aysta et al. |
| 5,061,452 A | 10/1991 | Yamamoto et al. |
| 5,101,967 A | 4/1992 | Sibley |
| 5,143,104 A | 9/1992 | Iba et al. |
| 5,181,604 A | 1/1993 | Ohta et al. |
| 5,269,671 A | 12/1993 | McCormick |
| 5,281,227 A | 1/1994 | Sussman |
| 5,388,686 A | 2/1995 | Kanner et al. |
| 5,409,833 A | 4/1995 | Hu et al. |
| 5,424,040 A | 6/1995 | Bjornsson |
| 5,427,742 A | 6/1995 | Holland |
| 5,518,612 A | 5/1996 | Kayal et al. |
| 5,532,168 A | 7/1996 | Marantz |
| 5,533,642 A | 7/1996 | Lafond et al. |
| 5,543,114 A | 8/1996 | Dudek |
| 5,558,846 A | 9/1996 | Alvord et al. |
| 5,609,827 A | 3/1997 | Russell et al. |
| 5,665,398 A | 9/1997 | McCormick |
| 5,681,740 A | 10/1997 | Messier et al. |
| 5,817,032 A | 10/1998 | Williamson, IV et al. |
| 5,928,935 A | 7/1999 | Reuss, Jr. et al. |
| 5,941,260 A | 8/1999 | Wershe |
| 6,017,476 A | 1/2000 | Renshaw |
| 6,074,614 A | 6/2000 | Hafeman et al. |
| 6,204,375 B1 | 3/2001 | Lader |
| 6,248,535 B1 | 6/2001 | Danenberg et al. |
| 6,256,089 B1 | 7/2001 | Baker |
| 6,375,028 B1 | 4/2002 | Smith |
| 6,513,673 B2 | 2/2003 | Alley |
| 6,899,850 B2 * | 5/2005 | Haywood et al. ............. 422/547 |
| 7,001,724 B1 * | 2/2006 | Greenfield ............... 435/270 |
| 7,147,826 B2 * | 12/2006 | Haywood et al. ............. 422/547 |
| 8,071,058 B2 * | 12/2011 | Haywood et al. ............. 422/559 |
| 2001/0017271 A1 | 8/2001 | Yavitz |

* cited by examiner

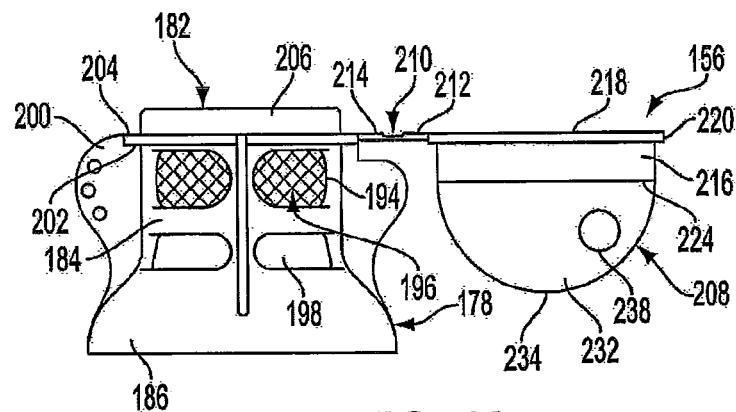
FIG. 19
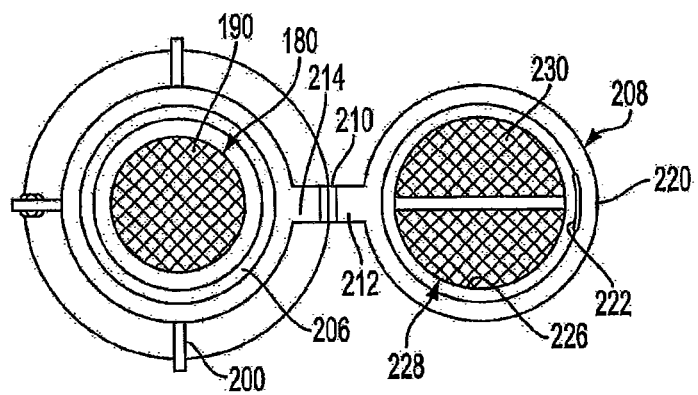
FIG. 20
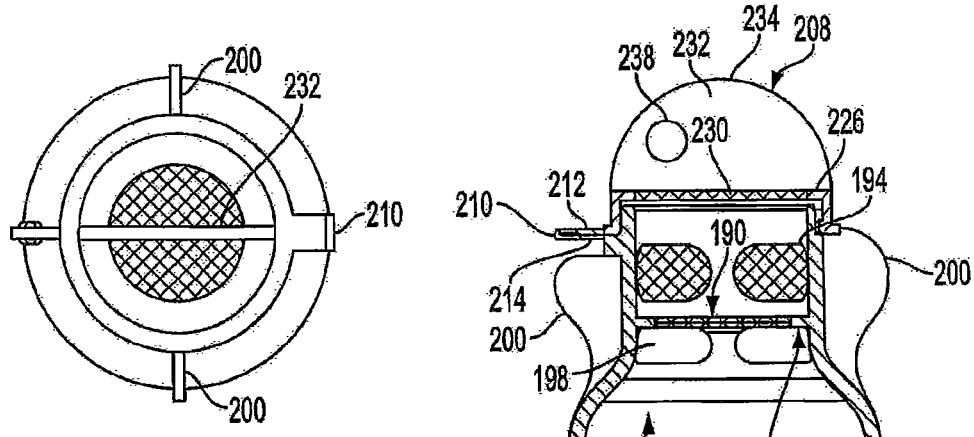
FIG. 21
FIG. 22

APPARATUS FOR TRANSPORTING BIOLOGICAL SAMPLES

CROSS-REFERENCE TO RELATED APPLICATIONS

This application is a divisional of U.S. patent application Ser. No. 11/534,880, filed Sep. 25, 2006, entitled "Apparatus for Transporting Biological Samples", which is a continuation of U.S. patent application Ser. No. 10/269,094, filed Oct. 11, 2002, which in turn claims priority to U.S. Provisional Application No. 60/328,407, filed Oct. 12, 2001, the disclosures of each of which are hereby incorporated by reference.

BACKGROUND OF THE INVENTION

1. Field of the Invention

The present invention is directed to a method and apparatus for collecting, transporting, processing and storing biological samples in a reagent. The invention is also directed to a method and apparatus for transporting biological samples where the biological samples are completely immersed in a reagent.

2. Description of Related Art

Biological samples are often obtained by a researcher or clinician for diagnostic evaluation to determine the presence of certain diseases and to determine an appropriate treatment for the disease. Common diagnostic processes for diseases include histological and cytological diagnosis. For example, tumors are typically examined for histological and cytological abnormalities.

Biological samples are also obtained for molecular diagnostic. In recent years, nucleic acid analysis, and particularly RNA and DNA analysis and studies have become common place in research for the treatment of numerous diseases. An essential requirement for accurate RNA and DNA qualitative and quantitative analysis is the presence of high quality and intact RNA and DNA. For example, intact nucleic acid is necessary for RT-PCR, Northern blot hybridization and nuclease protection assays analysis of nucleic acid expressions.

Biological samples can be obtained from various sources and by various processes. Numerous devices exist that are designed to remove a small amount of tissue from an organ or specimen. For example, small samples can be obtained using a device similar to a punch to extract core fragments of tissue. Another device for performing a biopsy uses an aspirating needle device that can extract single cells, small cell clumps and tissue fragments.

Generally, it is preferable to perform the histologic or cytologic analysis immediately after being extracted from the patient or source to obtain the most accurate results possible. Numerous molecular changes can occur in the sample during storage, which can affect the final results. For example, nucleic acids in a biological sample can undergo numerous changes, including gene transcription, and the nucleic acids readily degrade during storage at room temperature when not treated with a stabilizing agent.

The analysis of a biological sample at the time of collection is often impossible or not practical. Therefore, it is necessary to store the sample under controlled conditions to prevent or inhibit degradation of the tissue components and to retain the integrity of the results of the analysis. Biological samples are typically stored in a container with a suitable fixative reagent. A typical fixative reagent is 10% formaline. Other fixatives include water miscible alcohols, ethanol/acetone mixtures, and ethanol/acetic acid mixtures. Ammonium sulfate solutions have also been used as disclosed in U.S. Pat. No. 6,204,375 to Lader, which is hereby incorporated by reference in its entirety. The containers with the biological sample in the fixative reagent can then be sent to a pathology laboratory or other destination for analysis.

Proper handling of the biological sample is essential for accurate nucleic acid analysis, and particularly for RNA quantitative and qualitative evaluation. The biological samples require an effective amount of the fixative reagent to preserve the sample. In addition, some reagents require that the sample be completely covered with the fixative reagent to ensure effective preservation. Typically, the biological samples are simply placed in a small container for storage. The biological samples which can be very small can be difficult to locate and recover from the container.

To obtain high quality test results from biological specimens, early stabilization or preservation of the sample may be required. Biological samples and other cells can be quick frozen by various methods as known in the art. Specimens for anatomical pathology are typically preserved in formaldehyde and alcohol based solutions. Specimens for molecular testing have been preserved in these and other reagents, such as chaotropic salts.

Quick freezing of biological samples can be effective in stabilizing cellular and molecular characteristics. Samples are typically transported on dry ice. Quick freezing, however, is not always available or convenient. Typically, the collection location and processing laboratory are separated in location and time, which creates an impediment to stabilization.

The prior methods and containers for storing, transporting and stabilizing biological samples have experienced some success for the intended purposes, but have several known limitations. There is, however, a continuing need in the industry for an improved container and method for storing biological samples.

SUMMARY OF THE INVENTION

The present invention is directed to a method and apparatus for collecting, transporting, processing and storing biological samples in a reagent. The invention is also directed to a method and apparatus for treating a biological sample with a reagent where the sample is continuously immersed in the reagent.

Accordingly, one aspect of the invention is to provide a method for maintaining a biological sample in a stabilizing reagent for stabilizing nucleic acids. The method is particularly suitable for treating whole tissue and cells.

Another aspect of the invention is to provide a method and apparatus for treating a biological sample with a reagent where the biological sample can be easily recovered from the reagent.

A further aspect of the invention is to provide a method for collecting, storing, stabilizing, processing and/or transporting a biological sample in a suitable reagent while maintaining a critical ratio of sample and regent.

Another aspect of the invention is to provide a method for stabilizing a biological sample for nucleic acid isolation and molecular diagnostic evaluation.

A further aspect of the invention is to provide a method for storing a biological sample in a nucleic acid stabilizing agent for extended periods of time to obtain intact nucleic acid from the sample for the analysis of RNA expression.

Still another aspect of the invention is to provide a container assembly for storing a biological sample, where the container assembly is prefilled with a tissue stabilizing agent.

A further aspect of the invention is to provide a method and container assembly for harvesting, transporting and storing biological samples that is simple and easy to use.

Another aspect of the invention is to provide a container assembly that is able to accommodate biological samples of different sizes while contacting the biological samples with an effective amount of a reagent.

Still another aspect of the invention is to provide a method and apparatus for maintaining a biological sample in a liquid reagent where the volume of the sample and the volume of the reagent are maintained in a predetermined ratio sufficient to treat the biological sample.

A further aspect of the invention is to provide a biological sample container assembly having a sample receiving holder of a predetermined size to limit and control the size of the biological sample in relation to the amount of a reagent in the container where the reagent is included in an amount sufficient to treat the sample effectively.

Still another aspect of the invention is to provide a biological sample container assembly where the assembly reduces the likelihood of spilling the reagent when the sample is inserted into or removed from the assembly.

Another aspect of the invention is to provide a container assembly for treating a biological sample in a reagent where the container assembly includes a sample holder that fits within a container and is removable from the container.

Still another aspect of the invention is to provide a method and apparatus for supporting a biological sample in a liquid reagent within a container where the biological sample remains immersed in the reagent regardless of orientation of the container.

Another aspect of the invention is to provide a kit or packaged assembly of components for obtaining and treating a biological sample. The kit preferably includes a sample holder, a container for receiving the sample holder, an amount of a treating reagent, and surgical tools, such as a scalpel, forceps, and the like. The components of the kit are preferably clean and sterile and packaged in a suitable sterile packaging.

A further aspect of the invention is to provide a container assembly for receiving a biological sample where the assembly includes a container having a closure cap and a removable sample holder having an open top that is closed by the closure cap when coupled to the container. The sample holder can be tethered to the container or the closure cap. In one embodiment, the sample holder can be coupled to the container.

Another aspect of the invention is to provide a biological sample container assembly including a reagent container and a sample holder dimensioned to fit within the container with limited lateral and vertical movement of the sample holder within the container to retain the sample holder in a predetermined area within the container.

Another aspect of the invention is to provide a biological sample container assembly having a container and a removable sample holder within the container, where the sample holder includes a tissue receiving cavity positioned to retain a biological sample immersed in a stabilizing liquid.

A further aspect of the invention is to provide a method and apparatus for defining a containment area in a volume of a liquid where the containment area is oriented to remain immersed in the liquid regardless of the orientation of the apparatus.

A further aspect of the invention is to provide a biological sample container assembly including a container, a closure member and a removable sample holder, where the sample holder has at least one supporting leg and can be supported on an inner face of the closure member.

A still further aspect of the invention is to provide a biological sample container assembly including a container, a closure member and a sample holder, where the closure member includes a plunger to immerse a biological sample into the reagent within the container and to displace a predetermined amount of air from the container, thereby reducing the headspace above the reagent.

Another aspect of the invention is to provide a container assembly for a biological sample including a container and sample holder having a cavity enclosed by a permeable surface to enable the free flow of a reagent into the cavity around the biological sample. The permeable surface can be made from a permeable media, such as a mesh material, paper filter or porous membrane screen.

Another aspect of the invention is to provide a biological sample container assembly including a container and a sample holder where the sample holder includes a removable closure.

A further aspect of the invention is to provide a sample holder for a biological sample where the sample holder is dimensioned to fit within a container and where the holder includes a permeable portion to enable the free flow of a reagent into the holder.

Another aspect of the invention is to provide a biological sample holder having an open top and a closure pivotally coupled to the holder to close the vessel and where the holder cooperates with a container containing a reagent.

In one embodiment of the invention, the container assembly includes a container and sample holder that fits in the container and closure member. The sample holder is in the form of a platform-like device having an outer peripheral edge that nests on a ledge within a side wall of the container. The sample holder includes a recessed area for supporting a biological sample. The recessed area is formed by a permeably wall to allow the free flow of the liquid reagent through the recessed area. The closure member includes a body or plunger-like member that closes the open top end of the recessed area when coupled to the container. The sample holder includes a plurality of supporting legs for supporting the sample holder when removed from the container.

In another embodiment, the sample holder is a free standing device that is removable from the container. The sample holder is formed with a permeably side wall and a permeable bottom forming a cavity with an open top. A closure cap is coupled to the holder by a hinge for closing the cavity. The cap can include a tab extending upwardly to enable the operator to remove the sample holder from the container.

These and other aspects of the invention are basically attained by providing a container assembly for storing a biological sample. The container has a bottom, a side and an open top end. The container also has a dimension to contain a volume of a reagent sufficient to treat a biological sample. A closure member is provided for coupling to the open top end of the container. A sample holder is removable from the container and closure member and has an internal cavity with a dimension for receiving a biological sample. The holder has a plurality of fluid openings into the cavity to enable free flow of the reagent into the cavity. The sample holder also has a dimension to fit between the bottom and side of the container and the closure and to immerse the cavity in the reagent.

The aspects of the invention are further attained by providing a container assembly comprising a container having a bottom, a side and an open top end, and being dimensioned to contain a liquid reagent. A closure is removably coupled to the container and closes the open top end. The closure has an outer face and an inner face. A sample holder has an internal cavity for receiving a biological sample. The holder has at least one fluid opening into the cavity and has a dimension to fit within the container to completely immerse the cavity in the liquid reagent and to substantially prevent linear movement of the sample holder in the container. A body is coupled to the inner face of the closure to displace a portion of the liquid reagent in the container.

The aspects of the invention are still further attained by providing a method of stabilizing nucleic acids in cells and biological samples comprising the steps of providing a container having a bottom, a side and an open top end. The container contains a nucleic acid stabilizing reagent. A biological sample is placed in a sample holder. The sample holder has an internal cavity for receiving the biological sample and has a fluid opening into the cavity. The sample holder is positioned in the container and is completely immersed the internal cavity in the reagent. A closure member is placed on the container to close the container. The closure member cooperates with the sample holder to limit movement of the sample holder within the container and to retain the internal cavity immersed in the reagent.

The various aspects, advantages and other salient features of the invention will become apparent from the annexed drawings and the following detailed description of the invention.

BRIEF DESCRIPTION OF THE DRAWINGS

The following is a brief description of the drawing, in which:

FIG. 19 is a side view of the sample holder of the embodiment of FIG. 18;

FIG. 20 is a top view of the sample holder of the embodiment of FIG. 19 in the open position;

FIG. 21 is a top view of the closed sample holder;

FIG. 22 is a cross-sectional side view of the sample holder;

DETAILED DESCRIPTION OF THE INVENTION

Figure 1:
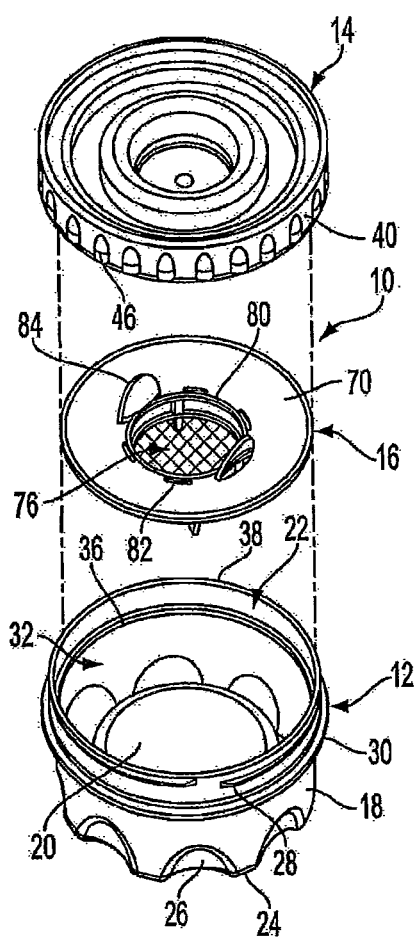
FIG. 1 is an exploded perspective view of the container assembly in a first embodiment.

The present invention is directed to a method and apparatus for collecting, transporting, processing and storing biological samples. The invention is also directed to a method and apparatus for collecting, transporting, processing and storing biological samples in a liquid reagent where the samples are completely immersed in the reagent.

The method and apparatus of the invention are particularly suitable for transporting biological samples, such as biological samples intended for molecular diagnostic processes. The biological samples are retained in a container assembly that contains a suitable reagent, such as, for example, a liquid stabilizing agent, so that the biological sample remains completely immersed in the reagent regardless of the orientation of the container. In other embodiments, the reagent can be a gel, solid or semi-solid which can be in the form of beads or other particles. The solid of gel can be used alone or in combination with a liquid reagent.

The invention is particularly directed to a method of treating a biological sample with a suitable reagent in a container. The method ensures that the sample contacts an amount of the reagent effective to treat the sample and to maintain the sample immersed in the reagent to prevent or minimize contact of the sample with air. In one embodiment, a container is filled to a predetermined level with a liquid reagent so that when the sample is placed in the container, the sample displaces a portion of the reagent and raises the level of the reagent to a level sufficient to completely immerse the sample without spilling the reagent. Preferably, the sample is retained in a predetermined location or area in the internal cavity of the container so that the sample remains immersed in the reagent regardless of the orientation of the container.

In one embodiment, the method of treating a biological sample with a reagent includes the steps of collecting a biological sample and immediately placing the sample in the reagent. Typically the sample is completely immersed in the reagent without any intermediate steps. Preferably the sample is completely covered by or immersed in the reagent as soon as possible after collection to minimize contact with the air. The sample is retained in a retaining area in a container that contains the reagent so that the sample remains immersed during handling and transporting of the container without the sample being exposed to the air.

Referring to FIGS. 1-10, the invention, in a first embodiment, is directed to a container assembly 10. Container assembly 10 includes a container 12, a closure cap 14 and a sample receiving holder 16.

In the embodiment illustrated, container 12 has a substantially cylindrical shape formed by a side wall 18 and a bottom wall 20. Side wall 18 extends from an open top end 22 of container 12 to a bottom edge 24. A plurality of recessed areas 26 are formed in side wall 18 adjacent bottom edge 24. Recesses 26 have a dimension to assist the operator in gripping the container for assisting the operator in opening and closing container assembly 10.

Side wall 18 includes external threads 28 adjacent open top end 22 for mating with complementing threads on cap 14. A rib 30 extends radially outward from side wall 18 and is spaced axially from open top end 22. Rib 30 preferably is spaced from open top end 22 a distance complementing the dimensions of closure cap 14 and encircles container 12.

Figure 4:
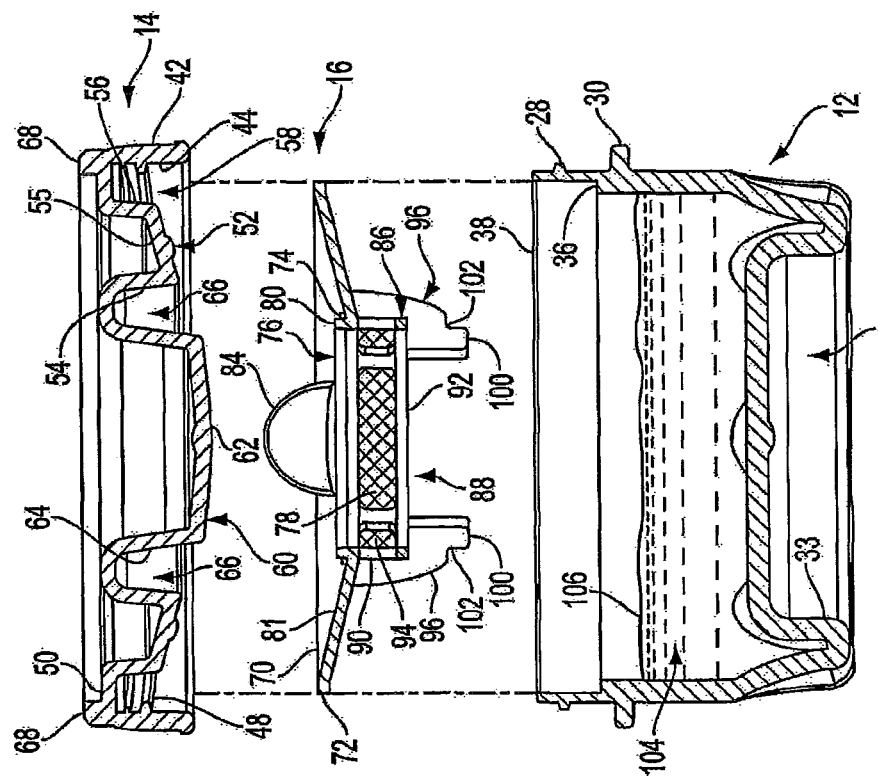
FIG. 4 is an exploded cross-sectional side view of the container assembly.

Referring to FIG. 4, container 12 has an internal cavity 32 with a dimension sufficient to contain an effective amount of a liquid stabilizing agent sufficient to stabilize a biological sample. In the embodiment illustrated, bottom wall 20 is spaced from bottom edge 24 of side wall 18 by a cylindrical portion 33 to form a recess 34 in the bottom of container 12. In alternative embodiments, the bottom of container 12 can be substantially flat.

Side wall 12 includes a ledge 36 extending in a substantially radial direction with respect to a center axis of container 12. Ledge 36 has a width sufficient to support sample holder 16 as discussed hereinafter in greater detail. In the embodiment illustrated, ledge 36 is positioned at the upper end of side wall 18 and is oriented substantially parallel to a top edge 38 of container 12. Preferably, ledge 36 is formed in side wall 18. In alternative embodiments, a rib can extend inwardly from the inner face of side wall 18 a distance to support sample holder 16.

Figure 3:
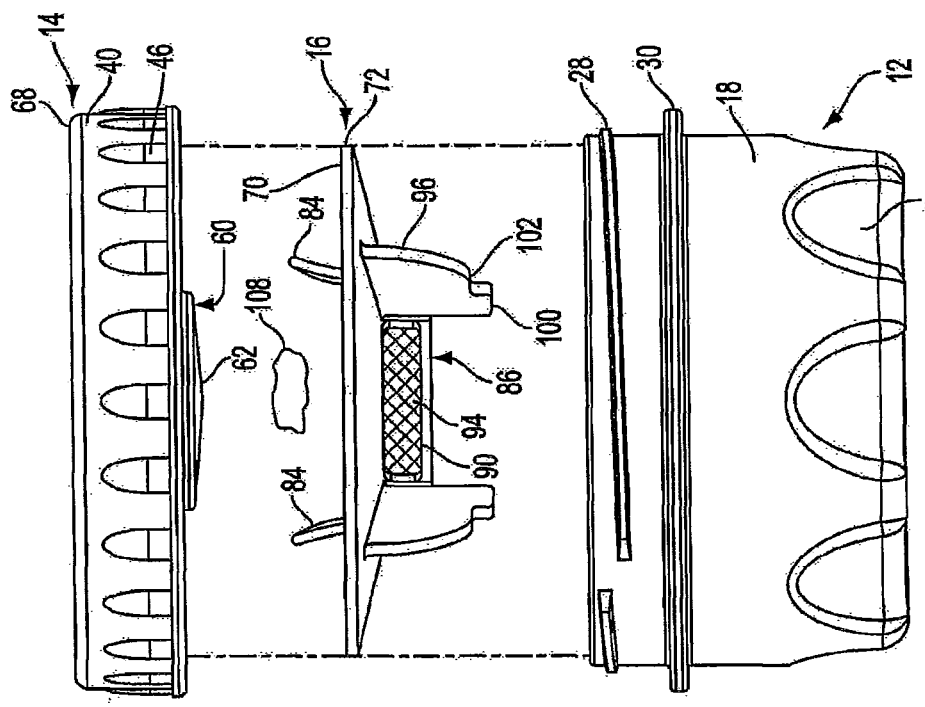
FIG. 3 is an exploded side view of the assembly of FIG. 1.

Cap 14 has a dimension complementing side wall 18 of container 12 for mating with container 12. As shown in FIGS. 3 and 4, cap 14 includes a side wall 40 having a substantially cylindrical shape with an outer surface 42 and an inner surface 44. As shown in FIG. 3, outer surface 42 includes a plurality of dimples 46 to assist the operator in handling cap 14. Inner surface 44 includes threads 48 for mating with threads 28 of container 12.

Cap 14 includes a top wall 50 coupled to side wall 40. An annular rib 52 extends in a generally downward, axial direction with respect to cap 14 from top wall 50. Rib 52 includes an inner axial side wall 54 and an outer axial side wall 56 connected by bottom wall 55. As discussed hereinafter, bottom wall 55 of rib 52 is oriented to contact sample holder 16 while in container 12 to limit movement of sample holder 16. Outer axial side wall 56 extends substantially parallel to side wall 40 and is spaced inwardly from side wall 40 a distance to form a recess 58 for mating with top edge 38 of container 12.

Top wall 50 of cap 14 includes a centrally located body defining a plunger 60 having a substantially frustoconical shaped bottom wall 62 and an annular side wall 64 extending between top wall 50 and bottom wall 62. As discussed hereinafter, plunger 60 defines a closure member for sample holder 16. As shown in FIG. 4, side wall 64 of plunger 60 has an axial length slightly greater than the axial length of side wall 40 and rib 52 so that bottom wall 62 of plunger 60 is spaced axially outward from the bottom edge of side wall 40. Side wall 64 of plunger 60 is spaced from inner axial side 54 of rib 52 to form an annular shaped recess 66. In one preferred embodiment, side wall 64 of plunger 60 has a slightly tapered frustoconical shape.

An annular lip 68 extends upward from top wall 50 adjacent the outer edge in an axial direction as shown in FIG. 4. Lip 68 forms a ledge with top wall 50 and is dimensioned to complement bottom edge 24 of side wall 18 of container 12. In this manner, several container assemblies 10 can be stacked vertically with the bottom edge 24 of wall 18 received in the area defined by lip 68.

Figure 2:
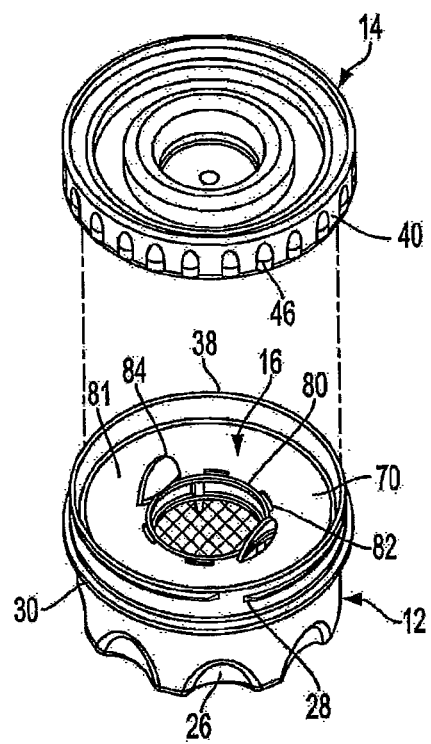
FIG. 2 is an exploded perspective view of the container assembly showing the sample holder received in the container.

Sample holder 16 is dimensioned to be received in container 12 and to support a biological sample. Sample holder 16 in the embodiment of FIGS. 1-10 includes a top wall 70 having a circular outer edge 72 and an inner edge 74. Inner edge 74 defines a central opening 76 into a cavity 78 for receiving a biological sample. Outer edge 72 of top wall 70 has a dimension complementing the inner dimension of container 12. An annular ridge 80 extends axially upward from a top face 81 of top wall 70 adjacent inner edge 74 and encircles central opening 76. A plurality of openings 82 are formed in top wall 70 adjacent annular ridge 80 as shown in FIGS. 1 and 2. A pair of tabs 84 is coupled to top wall 70 and extend in a substantially axial direction with respect to top wall 70 from top face 81. Tabs 84 have a dimension and are oriented to enable the operator to lift and manipulate sample holder 16.

Cavity 78 of sample holder 16 is formed by a body 86 having an open bottom end 88 and a plurality of side openings 90. Open bottom end 88 includes a permeable material, such as a screen or porous mesh 92, to define a bottom end of cavity 78. Side openings 90 also include a permeable or porous mesh 94 to form porous sides of body 86. Preferably, porous mesh 92 and 94 are made from a nylon mesh having a pore size to retain a biological sample in cavity 78 and to allow liquid to pass through. Other permeable materials, such as filter paper, can be used to enclose cavity 78 and retain the biological sample.

A plurality of legs 96 extend downwardly from a bottom face 83 of top wall 70 and are integrally formed with body 86. In the embodiment illustrated, legs 96 have a generally planar configuration and are oriented in a plane extending radially outward from a center axis of sample holder 16. Legs 96 are spaced apart a distance to support and stabilize sample holder 16 when placed on a horizontal surface.

Preferably, legs 96 have an axial length greater than an axial length of body 86 and extend beyond body 86 in an axial direction as shown in FIGS. 3 and 4. Legs 96 have a top end 98 coupled to top wall 70 and a bottom end 100 with a notch 102 formed along the bottom and the outer edge of legs 96.

Container assembly 10 is preferably made of a suitable plastic material that is non-reactive with the stabilizing agents and does not interfere with the biological sample. The components of container assembly 10 are generally made by a suitable injection molding process as known in the art.

In one embodiment of the invention, container assembly 10 is prefilled with a liquid reagent 106. Container assembly 10 is sealed, packaged and shipped to the physician or clinician for receiving and transporting a biological sample. Container assembly 10 can include a suitable seal or tamper indicator. In other embodiments, container assembly 10 can be packaged without a reagent and shipped to the consumer empty. Cap 14 is removed and container 12 is filled with a suitable reagent at the time of use. In one embodiment, container 12 is prefilled with the reagent 106 and sample holder 16 is packaged separately in a suitable sterile package. The sample holder is removed from the sterile package and the biological sample is placed in the holder. The container with the reagent is removed from its sterile package and the sample holder with the biological sample is placed in the reagent.

Figure 10:
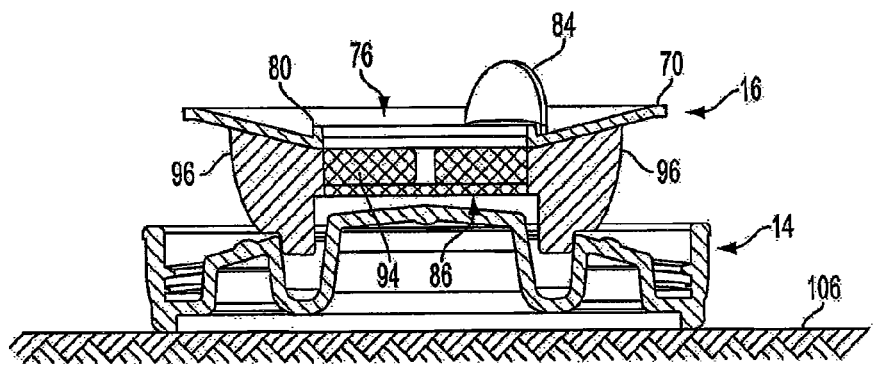
FIG. 10 is a cross-sectional side view of the sample holder support on the closure member.

In use, the operator removes cap 14 to expose sample holder 16. Cap 14 can be inverted and placed on a horizontal surface 106 as shown in FIG. 10. Sample holder 16 is then removed from container 12 by gripping tabs 84 and lifting upwardly to remove sample holder 16 from the reagent. Bottom end 100 of legs 96 of sample holder 16 are oriented to nest in recess 66 of cap 14 as shown in FIG. 10. In this manner, the liquid reagent adhering to sample holder 14 will drain into the recesses of cap 14. In addition, bottom end 100 of legs 96 engage recess 66 of cap 14 to stabilize sample holder 16 during use.

A biological sample 108 is then placed in cavity 78 of sample holder 16. In alternative embodiments, sample holder 16 can remain in container 12 and biological sample 108 deposited directly into cavity 78 and into reagent 106. Typically, it is desirable to separate sample holder 16 from container 12 at the time the biological sample is placed in sample holder 16 to prevent splashing of the reagent.

Figure 5:
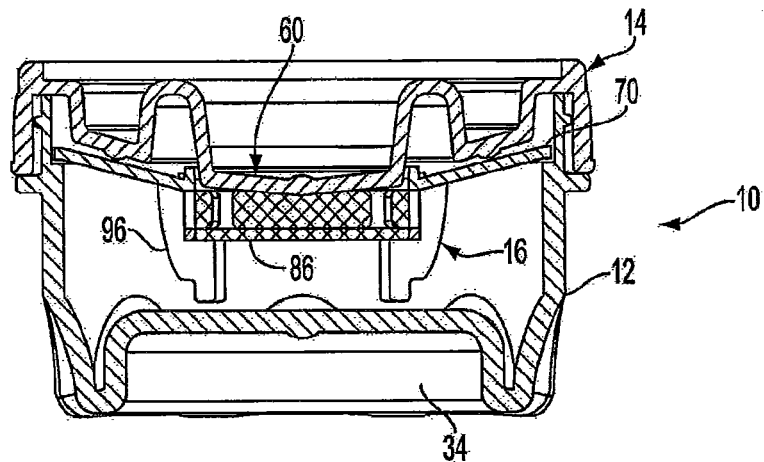
FIG. 5 is a cross-sectional view of the assembled container assembly.
Figure 6:
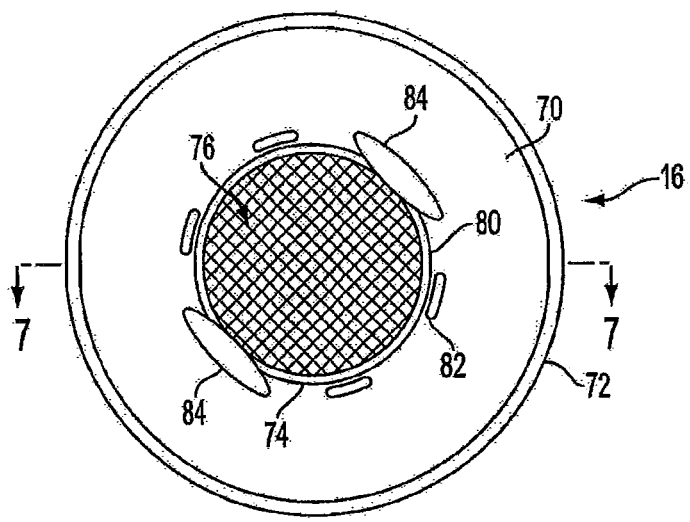
FIG. 6 is a top view of the sample holder.
Figure 7:
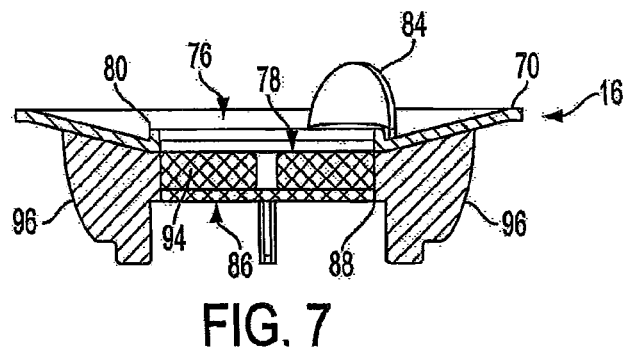
FIG. 7 is a cross-sectional view of the sample holder of FIG. 6 taken along line 7-7 of FIG. 6.
Figure 8:
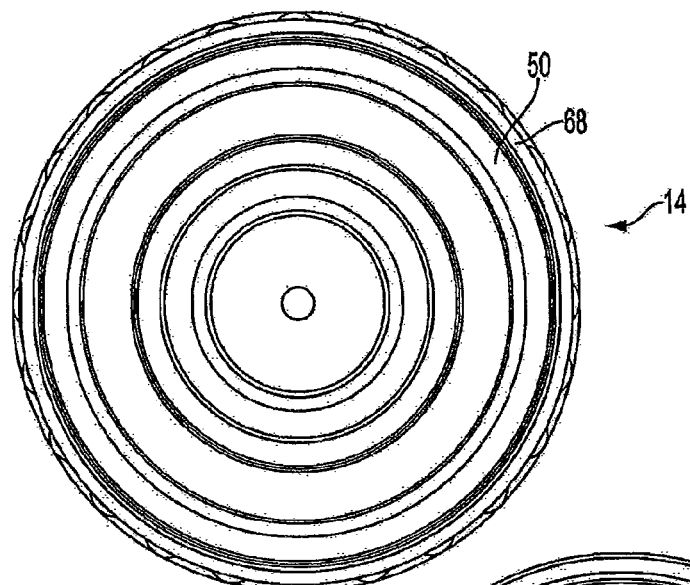
FIG. 8 is a top view of the closure member of the container.
Figure 9:
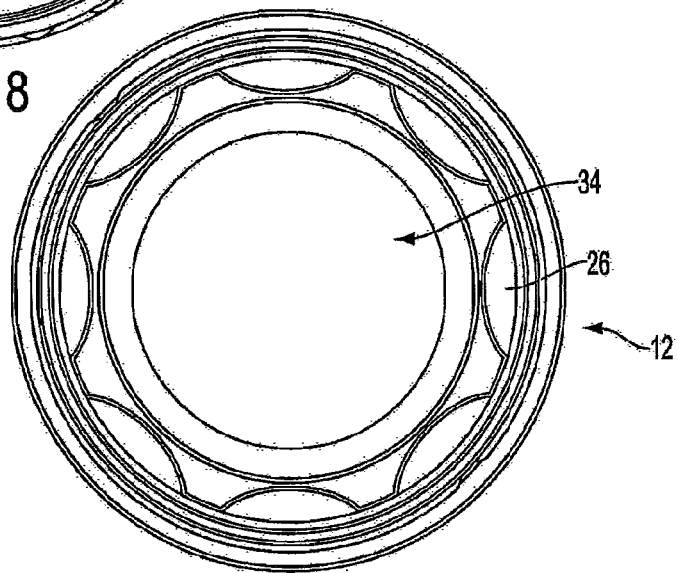
FIG. 9 is a bottom view of the container.

As shown in FIG. 5, outer edge 72 of top wall 70 of sample holder 16 is supported by ledge 36 of container 12. In the illustrated embodiment, container 12 and sample holder 16 are dimensioned so that bottom end 100 of legs 96 is spaced from bottom wall 20 of container 12. Outer edge 72 of top wall 70 has a dimension complementing the inner dimension of side wall 18 to limit movement of sample holder 16 within container 12.

In alternative embodiments, legs 96 can rest on bottom wall 20 of container 12 to support the sample holder 16 within the container 12. In this embodiment the side wall of the container can be formed without the ledge. The outer dimension of top wall 70 of sample holder 16 has a dimension to fit in the container and limit lateral movement between the side of the container.

With sample holder 16 positioned in container 12, cap 14 is mated with container 12 to close open top end 22. As shown in FIG. 5, plunger 60 of cap 14 has a dimension complementing opening 76 in top wall 70 of sample holder 16. Plunger 60 effectively closes cavity 78 to retain biological sample 108 in cavity 78 when cap 14 is coupled to container 12. Bottom wall 55 of rib 52 engages sample holder 16 as shown in FIG. 5 to limit axial movement of sample holder 16 within container 12.

As shown in FIG. 5, plunger 60 is oriented to extend inwardly into container 12 in an axial direction below top end 22 of side wall 18. As cap 14 is threaded onto container 12, plunger 60 displaces a volume of air and a volume of the reagent and reduces the head space above reagent 106 while closing central opening 76 of top wall 70. Plunger 60 is preferably dimensioned to push biological sample 108 downwardly into reagent 106 to retain biological sample 108 immersed in reagent 106 and to raise the level of reagent 106 within container 12. Preferably plunger 60 has a dimension to form a retaining area in cavity 78 in a location so that the sample remains immersed in the reagent.

Container assembly 10 is particularly suitable for containing a liquid reagent for preserving and stabilizing a biological sample. To ensure adequate contact of biological sample 108 with reagent 106, body 86 of sample holder 16 preferably includes permeable mesh 92 and 94 to allow continuous circulation of reagent 106 through cavity 78. The volume of reagent 106 necessary to effectively treat biological sample 108 can depend on the nature and concentration of the stabilizing agent. In preferred embodiments, the ratio of the volume of container 12 to the volume of cavity 78 is at least 5:1, and typically ranges from about 5:1 to about 12:1. Preferably, the ratio of the volume of stabilizing agent 104 in container 12 to the volume of cavity 78 containing biological sample 108 is about 10:1. This ensures a suitable ratio of at least 10:1 of the volume of the reagent and the biological sample.

Cavity 78 of sample holder 16 has a dimension to contain an appropriate size and dimension of a biological sample. In one embodiment, cavity 78 is about 2 cm in diameter and about 0.75 cm deep. Preferably, cavity 78 has a dimension to receive a sample having at least one dimension ranging from 1 mm to about 5 cm. For example, cavity 78 can have a dimension to receive a core needle biological sample having a length of about 3 cm and a diameter of about 1-2 mm. Cavity 78 can also be dimensioned to receive larger samples ranging from about 3.5 cm to about 5 mm in at least one dimension.

Biological sample 108 can be removed from sample holder 16 by removing cap 14 to expose cavity 78. Typically, cap 14 is placed on a horizontal surface 106 as shown in FIG. 10 and sample holder 16 is removed from container 12 and placed on cap 14. Permeable mesh 92 and 94 preferably have a sufficiently small pore size to enable holder 16 to strain small pieces of the biological sample. Top wall 70 of sample holder 16 has a generally frustoconical shape and is inclined in a generally downward direction toward central opening 76. Reagent 106 is directed along top wall 70 toward drain openings 82. Reagent 106 is collected in the recesses of cap 14 and is either discarded or poured back into container 12. Biological sample 108 then can be readily removed from cavity 78 and analyzed according to standard analytical processes as known in the art.

The method of the invention contacts a biological sample with a treating reagent in a minimum predetermined ratio to ensure contact of the tissue sample with an effective amount of the reagent sufficient to treat the sample. The volume of the tissue sample is controlled in relation to the amount of the reagent to regulate the relative amount of the biological sample to the amount of the reagent. In preferred embodiments of the invention, the ratio of the relative volume of the reagent to the biological sample is at least 5:1. Typically, the ratio of the volume of reagent to the volume of the biological sample is at least about 10:1. The critical amount of the reagent to treat a biological sample effectively can vary depending on the particular sample and the particular reagent. The amount of reagent required to treat a sample effectively is affected by the weight, volume and density of the sample. For example, some tissue samples are dense compared to other tissues and may require more or less of a particular reagent than that required by a less dense or porous tissue.

The biological samples that are treated by the methods of the invention are typically tissue samples. Examples of biological samples that can be treated include organ specimens, tumor specimens, bone specimens, and connective tissue specimens, such as tendons and membranes.

The reagent for treating the biological sample is preferably a liquid but can be a gel or viscous material. The treating reagent is typically an aqueous or alcohol solution containing a suitable reagent, such as a stabilizing agent or fixative reagent. Examples of suitable reagents including stabilizing agents, lysing agents, drying agents, preservation reagents, and cationic detergents. The reagents can be organic or inorganic compounds. In one embodiment, the reagent is a 10% by volume aqueous formaline solution.

The method and apparatus of the invention are particularly suitable for use in transporting a biological sample to another location, such as to a remote laboratory, while stabilizing and preserving the sample. The method of the invention in one embodiment collects a biological sample, such as a tissue sample, and immediately places the sample in the container assembly to immerse the sample in the reagent contained within the container assembly. The container assembly is able to retain the biological sample immersed in the reagent while being transported and to provide an amount of the reagent sufficient to treat the sample. In one embodiment, the reagent is a nucleic acid stabilizing reagent that is able to preserve the nucleic acids in the cells of the sample for extended periods of time. Preferably, the sample is collected and immediately immersed in the stabilizing reagent to enable high quality quantitative and qualitative analysis of the nucleic acids.

The reagent is preferably an aqueous medium or alcohol containing one or more components for treating the biological sample. In one embodiment, the reagent is for stabilizing cells and biological samples. In one preferred embodiment, the preserving and stabilizing reagent is able to preserve nucleic acids for extended periods of time prior to isolation from the cells. The stabilizing reagent included in the container is an amount effective to penetrate the cells and biological sample to prevent or inhibit nucleases from decomposing the nucleic acids.

In one embodiment, the reagent is able to precipitate nucleic acids and the cellular protein in the sample to inhibit or inactivate the action of the nuclease. In this embodiment, the stabilizing agent is an aqueous medium containing a salt that is able to precipitate the nucleic acid and cellular proteins. Examples of suitable salts are sulfates, such as ammonium sulfate, ammonium bisulfate, cesium sulfate, cadmium sulfate, cesium iron (II) sulfate, chromium (III) sulfate, cobalt (II) sulfate, copper (II) sulfate, lithium sulfate, magnesium sulfate, manganese sulfate, potassium sulfate, sodium sulfate and zinc sulfate. The salt concentration can range from about 0.10 to 1.50 g/ml, and preferably about 0.7 g/ml. In other embodiments, the stabilizing agent can include formalin or a chaotropic salt such as quanidium compounds.

The reagent can also include amounts of ethanol, methanol, acetone, trichloracetic acid, propanol, polyethylene glycol, acetic acid and a chelating agent such as EDTA. Buffering agents such as sodium acetate can also be added. Generally, the stabilizing agent has a pH of about 4-8.

The reagents are generally liquids that can pass through the porous mesh of the sample holder to contact the biological sample. In other embodiments, the reagent can be a gel, solid or semi-solid in the form of beads or particles. The gel and the beads can be permeable or impermeable to the porous mesh of the sample holder. Typically the beads or particles have a particle size that is larger than the opening size of the mesh in the sample holder and are not permeable though the mesh. In embodiments where the gel or beads are impermeable to the mesh of the sample holder, the cavity of the sample holder can contain an amount of the gel, beads or particles to contact the biological sample. The dimensions of the cavity are selected to provide the necessary volume ratio of the biological sample to the reagent. The gel can be permeable to the permeable mesh of the sample holder to pass through the walls of the sample to contact and immerse the biological sample in the reagent. The solid or semi-solid reagent, such as beads or particles, can be used alone although they are typically used in combination with a liquid or gel reagent to supplement the solid or semi-solid reagent so the biological sample is maintained immersed in the reagents. In this embodiment, the cavity of the sample holder can contain the solid or semi-solid reagent and the container can contain the liquid or gel reagent that is permeable to the wall of the sample container. In this manner the biological sample is placed in the sample holder in contact with the solid or semi-solid reagent. The sample holder is then placed in the container with the liquid or gel reagent to enable the reagent to flow through the walls of the sample holder to fill the spaces between the beads or particles and to surround the biological sample.

Figure 11:
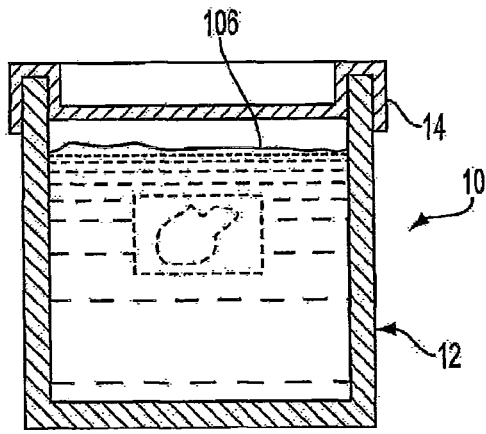
FIG. 11 is a cross-sectional side view of the container in an upright position depicting a containment area below the surface of the reagent.
Figure 12:
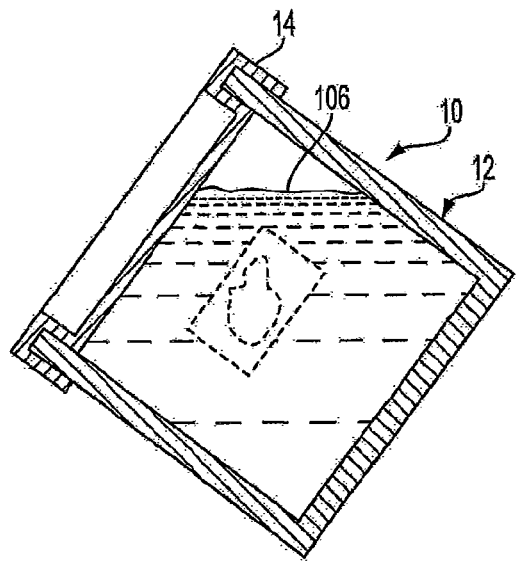
FIG. 12 is a cross-sectional side view of the container of FIG. 11 positioned at an incline.
Figure 13:
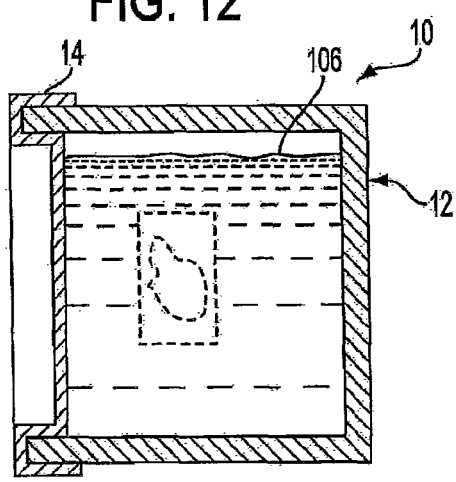
FIG. 13 is a cross-sectional side view of the container of FIG. 11 positioned on its side.

Container assembly 10 is constructed to define an internal containment area within container 12 to contain biological sample 108 in a predetermined area of container 12. Preferably, a containment area 109 is defined by cavity 78 of sample holder 16. Referring to FIGS. 11-13, sample containment area 109 is shown schematically by phantom lines in container 12. As shown in FIG. 11, containment area 109 is oriented in substantially the center of container 12 between the sides of container 12, cap 14, and bottom wall 20. As shown, reagent 106 is filled to a level to completely immerse containment area 109. Containment area 109 and reagent 108 are selected and controlled to maintain containment area 109 completely immersed in reagent 109 without regard to the orientation of container 12 as shown in FIGS. 12 and 13. In this manner, the biological sample will remain completely immersed in the reagent during handling and transporting of the container. Containing the biological sample in an area that is consistently below the level of the treating reagent regardless of the orientation of the container substantially prevents the biological sample from contacting the air in the container. Retaining the biological sample completely immersed in the treating reagent enhances complete treatment of the sample with the reagent and minimizes inaccuracies in the test results that can occur when the sample is exposed to air even for short periods of time. Certain reagents, such as nucleic acid stabilizing reagents, are most effective when the sample is immediately immersed in the reagent. Exposing the biological sample to air can lower the accuracy of the nucleic acid analysis.

EMBODIMENT OF FIGS. 14-17

FIGS. 14-17 illustrate a second embodiment of a container assembly 110 in accordance with the invention. Container assembly 110 includes a container 112, a closure cap 114 and a sample holder 116. Container 112 and cap 114 are substantially the same as container 12 and cap 14 of the embodiment of FIGS. 1-10 so that identical components are identified by the same reference number with the addition of a prime. In this embodiment, container 112 has a slight frustoconical shaped bottom wall and a substantially straight side wall.

Figure 14:
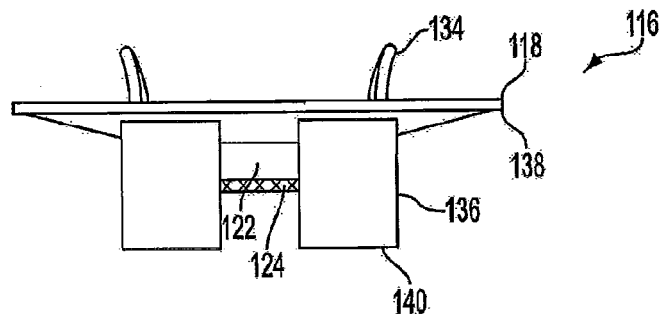
FIG. 14 is a side view of the sample holder in a second embodiment.
Figure 15:
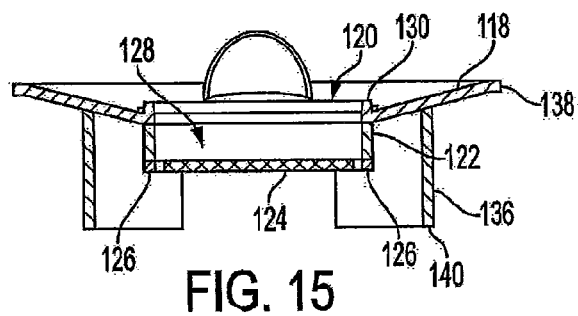
FIG. 15 is a cross-sectional view of the sample holder of FIG. 14.
Figure 16:
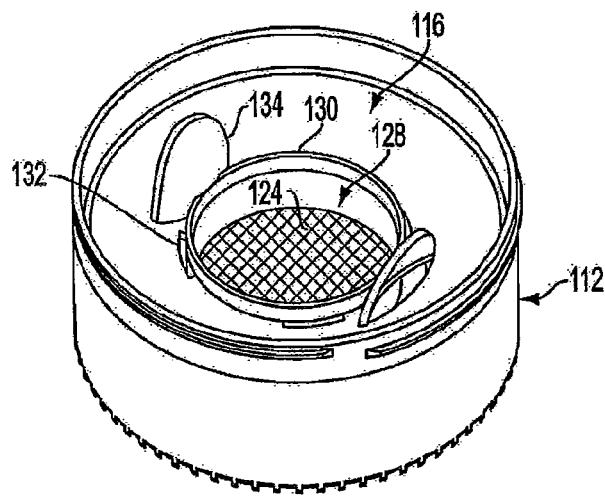
FIG. 16 is a perspective view of the sample holder of FIG. 14 and the container.

Sample holder 116 includes a top wall 118 having a substantially frustoconical shape converging toward a central opening 120 as shown in FIGS. 14 and 15. An annular wall 122 extends from top wall 118 around central opening 20 in a substantially upward axial direction. A liquid permeable mesh 124 is coupled to a bottom end 126 of annular wall 122 to define a cavity 128 for receiving a biological sample. An annular ridge 130 extends upward from central opening 120 in an axial direction. A plurality of drain openings 132 are formed in top wall 118 adjacent ridge 130. A pair of tabs 134 extends upwardly from the top face of top wall 118 for lifting and manipulating sample holder 116.

Figure 17:
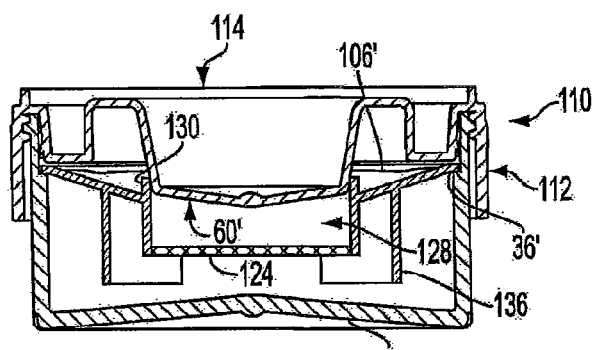
FIG. 17 is a cross-sectional side view of the container assembly including the sample holder of FIG. 14.

Legs 136 extend from the bottom face of top wall 118 downwardly in a generally axial direction. As shown in FIG. 17, legs 136 are spaced radially outward from annular wall 122 and have an axial length greater than the axial length of annular wall 122. Legs 136 in the embodiment illustrated have a substantially arcuate shape extending around a center axis and are oriented on opposite sides of sample holder 116 for supporting sample holder 116 in an upright position.

Sample holder 116 is dimensioned to fit within container 112 so that outer edge 138 of top wall 118 is nested in ledge 36' of container 112 as shown in FIG. 17. Preferably, legs 136 of sample holder 116 have a length so that the bottom ends 140 are spaced from bottom wall 20' of container 112. Cap 114 is coupled to container 112 so that plunger 60' closes cavity 128 and displaces air in container 112 to raise the level of the stabilizing agent above cavity 128 as shown in FIG. 17. Plunger 60' preferably has an axial length to push the biological sample downward into cavity 128 to retain the biological sample submerged in the reagent.

In the embodiments of FIGS. 1-10 and 14-17, a sample holder having a cavity for receiving a biological sample fits within a container for containing a liquid stabilizing agent. The sample holder is retained in the container by the closure cap. The closure cap closes the open top end of the cavity of the sample holder and closes the container in a manner to retain the biological sample completely immersed in the reagent. In preferred embodiments, the cap displaces a sufficient amount of air from the head space and displaces a portion of the reagent in the container to raise the level of the reagent above the cavity of the sample holder. In addition, displacing air in the head space above the reagent ensures that the biological sample is completely submerged in the reagent. Preferably, the container contains a sufficient amount of the reagent so that the biological sample remains immersed regardless of the orientation of the container assembly. The sample holder is pressed against the ledge in the side wall of the container to limit axial and lateral movement of the sample holder within the container. The cavity of the sample holder defines a containment area within the container to retain the biological sample below the surface of the reagent.

EMBODIMENT OF FIGS. 18-24

Figure 18:
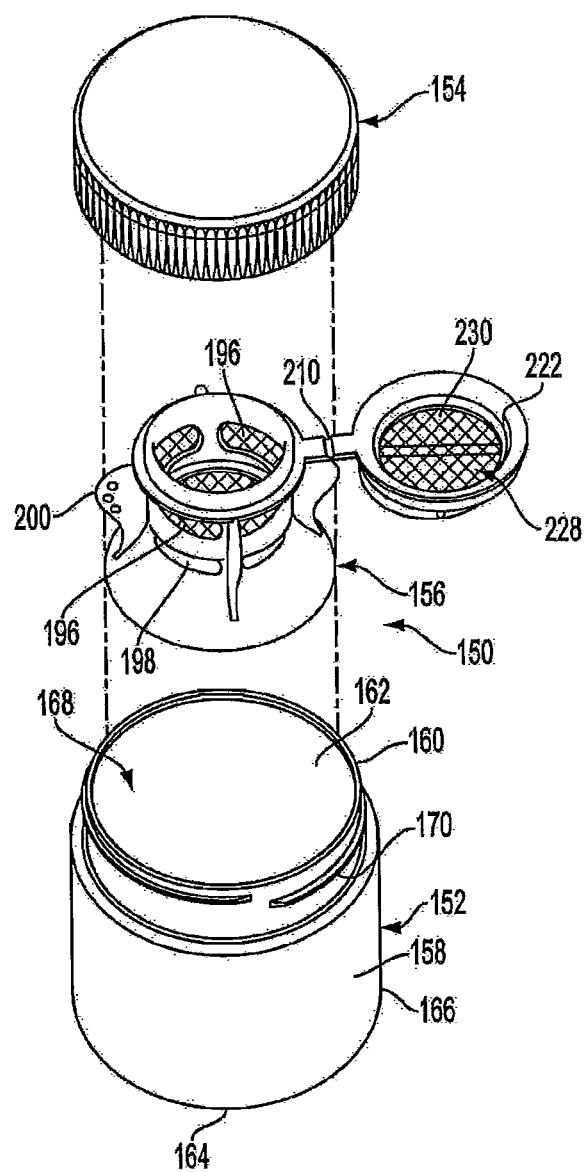
FIG. 18 is an exploded perspective view of the container assembly in another embodiment of the invention.

Another embodiment of the invention is shown in FIGS. 18-24. Referring to FIG. 18, container assembly 150 includes a container 152, a closure cap 154 and a sample holder 156.

Container 152 has a cylindrical side wall 158 having an upper end 160 defining an open top end 162. A bottom wall 164 is coupled to a bottom end 166 of side wall 158. Side wall 158 and bottom wall 164 define an internal cavity 168 for receiving sample container 156. Upper end 160 of side wall 158 includes threads 170 on the outer face for mating with cap 154.

Figure 23:
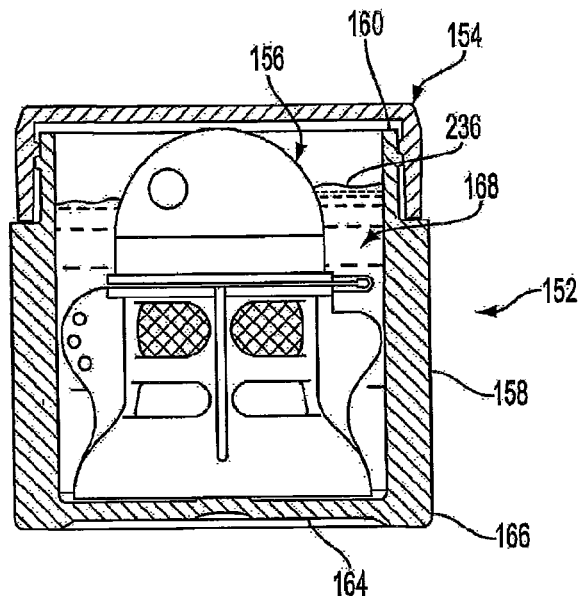
FIG. 23 is a side view of the sample holder in the container where the container is shown in cross-section.

Cap 154 has a top wall 72 and a depending side wall 174. Side wall 174 includes threads 176 on the inner face as shown in FIG. 23. Side wall 174 has a dimension to mate with upper end 160 of container 152.

Sample holder 156 is dimensioned to fit in container 152 and is easily removed from cavity 168. Preferably, sample holder 156 has a width to nest in container 152 to limit lateral and axial movement of sample holder 156 within container 152 when cap 154 is coupled to container 152. Referring to FIG. 23, sample holder 156 is retained within container 152 to limit movement of sample container 156 while contained within container 152.

Sample holder 156 has a body 178 having an internal cavity 180 and an open top end 182. Body 178 includes a side wall 184 extending from open top end 182 to a base 186. As shown in FIG. 19, base 186 is flared in a generally outward direction from side wall 184 to a substantially flat bottom.

Referring to FIG. 22, an internal ledge 188 extends radially inward from an inner surface of side wall 184. A permeable material such as a porous mesh 190 is coupled to ledge 188 to define a liquid permeable bottom of cavity 180. Ledge 188 and mesh 190 separate cavity 180 from a hollow portion 192 of base 186 and space cavity 180 from the bottom of container 152 when sample holder 156 is positioned in container 152.

Side wall 184 includes a plurality of spaced-apart openings 194 covered by a porous mesh 196 to enable a reagent to flow through cavity 180. Base 186 also includes a plurality of spaced-apart openings 198 to allow the flow of a liquid reagent into hollow portion 192 and through mesh 190 into cavity 180.

A plurality of tabs 200 extend radially outward from side wall 184 of body 178. In the embodiment illustrated, four tabs 200 are uniformly spaced around side wall 184. Tabs 200 have a generally flat planar configuration and are oriented in a plane extending in an axial direction and in a radial direction with respect to a center axis of body 178. As shown in FIG. 23, tabs 200 have an outer edge 202 defining a width of sample holder 156 and define the position of sample holder 156 within container 152. Tabs 200 function as stabilizing members to position sample holder 156 in container 152.

Side wall 184 of body 178 includes a radially extending flange 204 spaced from open top end 182 to define an annular collar 206. Sample holder 156 includes a closure member such as a cap 208 for closing open top end 182 of cavity 80. In a preferred embodiment, cap 208 is coupled to body 178 by flexible hinge 210. Preferably, cap 208 is integrally formed with body 178 by a suitable plastic molding process. Hinge 210 is coupled to cap 208 by a tab 212 and is coupled to flange 204 by a tab 214.

Cap 208 includes an annular side wall 216 having a bottom end 218 with an outwardly extending radial flange 220. Side wall 216 has an inner dimension complementing the outer dimension of collar 206. In the embodiment illustrated, side wall 216 includes a detent 222 on an inner surface for providing an interference fit of cap 208 with flange 204.

Side wall 216 includes a top end 224 with an inwardly extending radial flange 226. Flange 226 forms an opening 228 which is covered by a permeable mesh 230. A tab 232 forming a handle extends upwardly from flange 226 in an axial direction with respect to sample holder 156. Tab 232 includes a top end 234 defining a height of sample holder 156. Preferably, the height of sample holder 156 complements the height of container 152 so that when cap 154 is coupled to container 152, sample holder 156 is permitted limited axial movement within container 152 so that cavity 180 is retained within a predetermined area in container 152.

Figure 24:
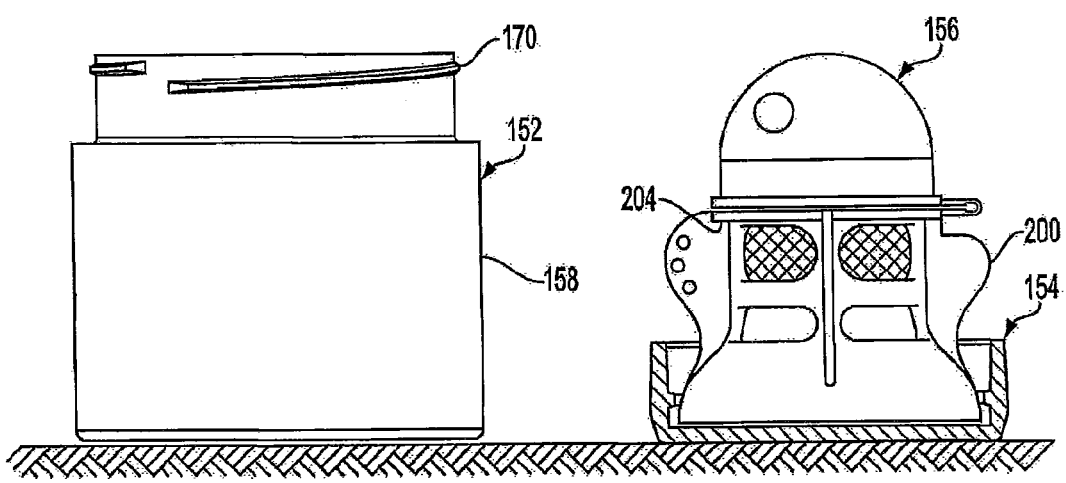
FIG. 24 is a side view of the container assembly showing the closure member supporting the sample holder.

In one embodiment, container 152 is prefilled with a liquid reagent at the time of assembly and packaging of container assembly 150. When ready to be used by the technician or scientist, cap 154 is removed from container 152 and placed on a horizontal surface as shown in FIG. 24. Sample holder 156 is removed from container 152 and placed in the inverted cap 154. In this manner, the stabilizing agent in cavity 180 can drain into cap 154. Cap 208 of sample holder 156 is opened by pivoting about hinge 210. A biological sample can then be placed in cavity 180. Cap 208 is pivoted to the closed position and snapped onto collar 206. Sample holder 156 is then replaced in container 152 so that cavity 180 is immersed in the liquid reagent 136 as shown in FIG. 23.

Sample holder 156 is dimensioned to contain a biological sample of sufficient size for analysis by standard procedures.

Preferably, cavity 180 has a dimension sufficient to receive the biological sample and is sufficiently open to the reagent to allow the stabilizing agent to flow through the cavity to ensure complete immersion of the biological sample in the reagent. Typically, the ratio of the volume of container 152 to the volume of cavity 180 is about 10:1. Tab 232 of cap 208 preferably has a dimension to be easily gripped by the technician using forceps or other tools for lifting sample holder 156 from container 152. An aperture 238 can be provided to assist in gripping tab 232 for manipulating sample holder 156.

EMBODIMENT OF FIGS. 25-28

FIGS. 25-28 show another embodiment of the container assembly 250 for receiving a biological sample. Container assembly 250 includes a container 252, a closure cap 254 for the container 252 and a sample holder 256.

Container 252 is similar to the container of the previous embodiments and includes cylindrical side wall 258 having an open top 260 with external threads 262 for mating with closure cap 254. Container 252 has a bottom wall and is dimensioned to receive sample holder 256 and to contain an effective amount of a treating liquid. Cap 254 has a top wall 266 and a side wall 268 with internal threads 270 for mating with threads 262 of container 252.

Figure 27:
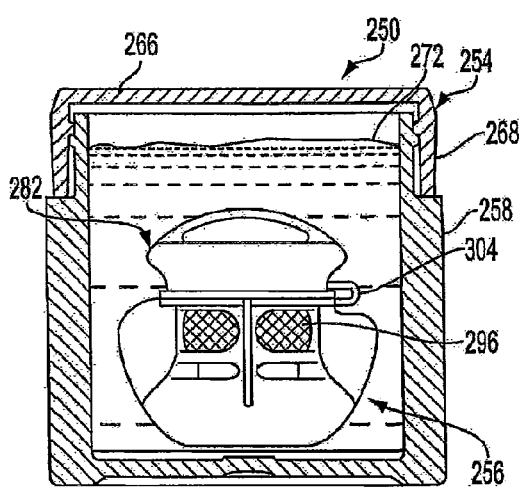
FIG. 27 is a side view in partial cross section of the container assembly of FIG. 27 in an upright position.
Figure 28:
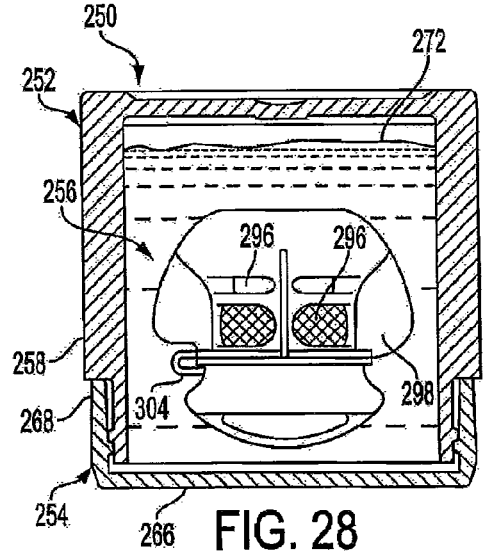
FIG. 28 is a side view in partial cross section of the container assembly of FIG. 27 in an inverted position.

Sample holder 256 in this embodiment has a density greater than the density of the treating reagent 272 so that sample holder 256 will sink in the reagent and remain in the bottom of the container in all orientations. As in the previous embodiments, sample holder 256 has a dimension to fit within container 252 as shown in FIGS. 27 and 28 and in cap 254 as shown in FIG. 26.

Figure 25:
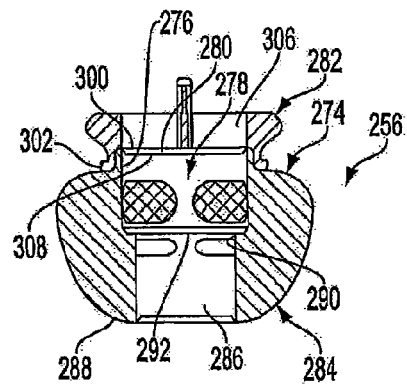
FIG. 25 is a cross-sectional side view of a sample holder in another embodiment of the invention.
Figure 26:
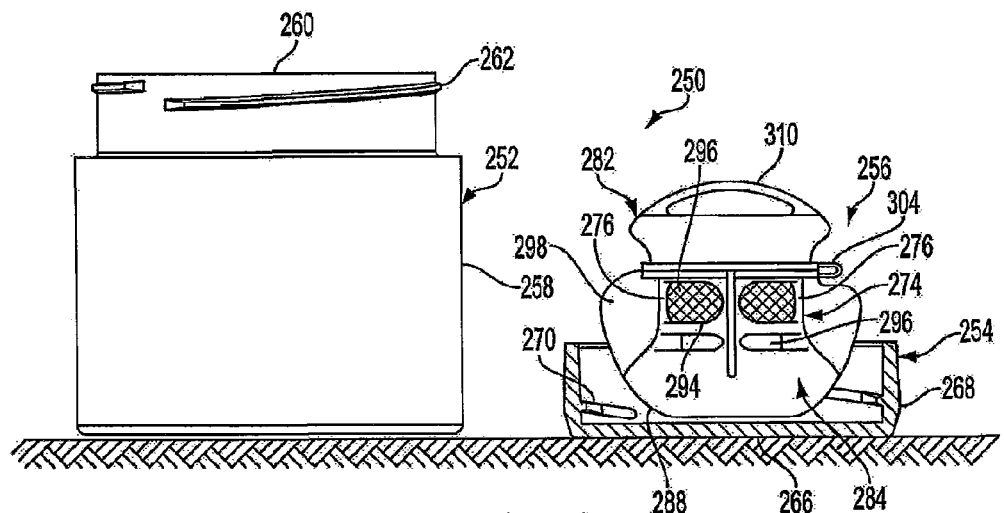
FIG. 26 is a side view of the container assembly of the embodiment of FIG. 25.

Referring to FIGS. 25 and 26, sample holder 256 has a body 274 formed by a side wall 276 defining an internal cavity 278. Body 274 has an open top end 280 that is closed by a removable closure member 282.

Body 274 of sample holder 256 includes a base 284 having an axial passage 186 and a slightly rounded bottom end 288. Base 284 defines a weighted portion to ensure that sample holder 256 sinks in the reagent 272. In the embodiment illustrated, side wall 276 includes an internal ledge 290 for supporting a permeable screen or mesh 292. Side wall 276 also includes a plurality of openings 294 that are closed by a permeable screen 296 to enclose internal cavity 278. A plurality of openings 296 are provided in body 274 to allow the flow of the reagent to axial passage 286.

A plurality of tabs 298 extend outwardly from side wall 276 of body 274. Tabs 298 have a planar configuration and are oriented in a substantially axial direction of body 274. Preferably, tabs 298 have a dimension to complement the inner dimension of container 252 to limit lateral movement of sample holder 256 within container 252.

Side wall 276 of body 274 includes a collar 300 for coupling with closure member 256. Closure member 282 has an annular wall 302 with an inner dimension complementing collar 300 for coupling closure member 282 to collar 300. Closure member 282 can be coupled to collar 300 by a friction fit or an interference fit. Preferably, closure member 282 is connected to body 274 by a flexible hinge 304 that is integrally molded with body 274 and closure member 282. Alternatively, a two-part hinge with a hinge pin can be used.

Closure member 282 is formed with an opening 306 in the top end and includes a liquid permeable mesh 308 to close opening 306. A handle 310 is coupled to closure member 282 to assist in lifting and manipulating sample holder 256.

Cavity 278 of sample holder 256 is dimensioned to contain a biological sample. Cavity 278 has an internal volume to limit the size of the biological sample so that the size of the biological sample is controlled in relation to the volume of the reagent in container 252. Preferably, ratio of the volume of the reagent in container 252 to the volume of the biological sample is at least 5:1, and preferably at least 10:1.

Container assembly 250 is used in a similar manner as in the previous embodiments. Sample holder 256 can be placed in cap 254 as shown in FIG. 26 so that the reagent can be collected. The closure member 282 is opened and a biological sample is placed in cavity 278 of sample holder 256. Sample holder 256 is closed and placed in container 252 containing reagent 272. Container 252 contains an amount of liquid reagent 277 to cover sample holder 256 in any orientation of container 252 as shown in FIGS. 27 and 28. Sample holder 256 has a density sufficient to sink to the bottom of container 252 regardless of the density of the biological sample contained in sample holder 256 as shown in FIGS. 27 and 28.

EMBODIMENT OF FIG. 29

Figure 29:
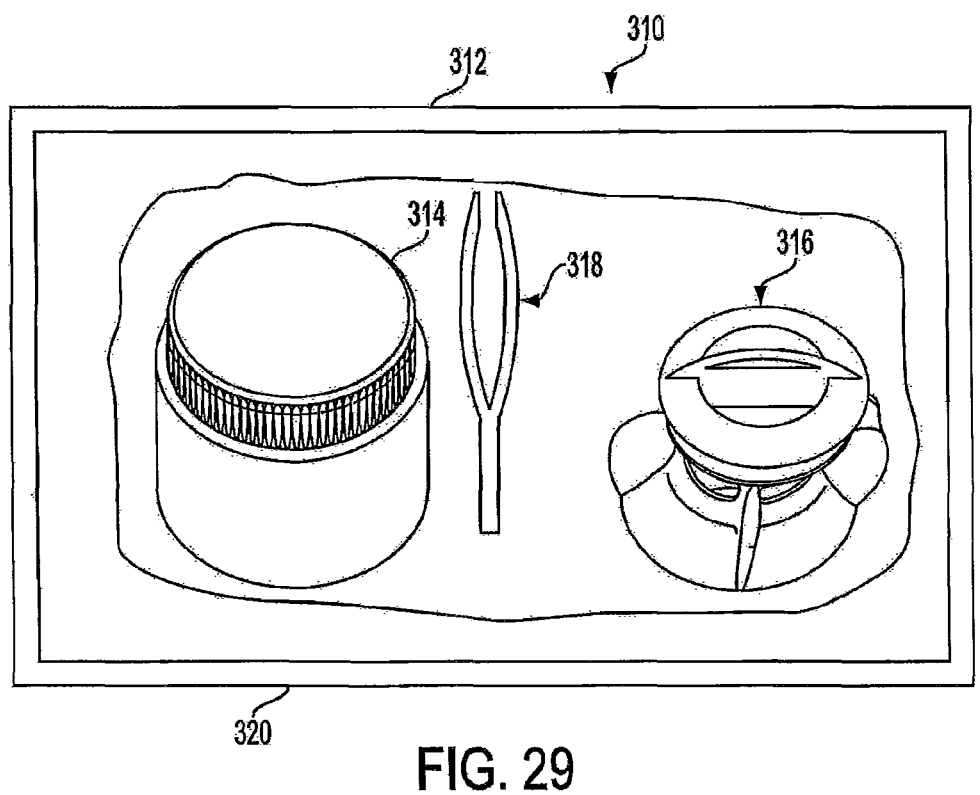
FIG. 29 is a front view in partial cross-section of a packaged kit including a container, a sample holder and forceps.

FIG. 29 shows an embodiment of the invention in the form of a prepackaged sterile kit 310 for use by the physician or clinician. The kit 310 includes a package 312 enclosing a container 314, a sample holder 316 and one or more tools, such as a pair of forceps 318. Preferably, the components are clean and sterile to be ready for use. Package 312 in the illustrated embodiment is a plastic pouch formed a sheet of plastic film or material that can be heat sealed around one or more of the edges 320. The heat sealed edges 320 can be formed as peel layers that can be readily separated by the operator to remove the contents.

In one embodiment, container 314 is prefilled with a liquid reagent and sample holder 316 packaged separately from container 314 as shown in FIG. 29. Alternatively, sample holder 316 is packaged in container 314 and removed from container 314 prior to use. In the embodiment illustrated, a pair of forceps is included in package 312, although other tools and surgical instruments can be included such as a scalpel and measuring gauge.

EMBODIMENT OF FIGS. 30 AND 31

Figure 30:
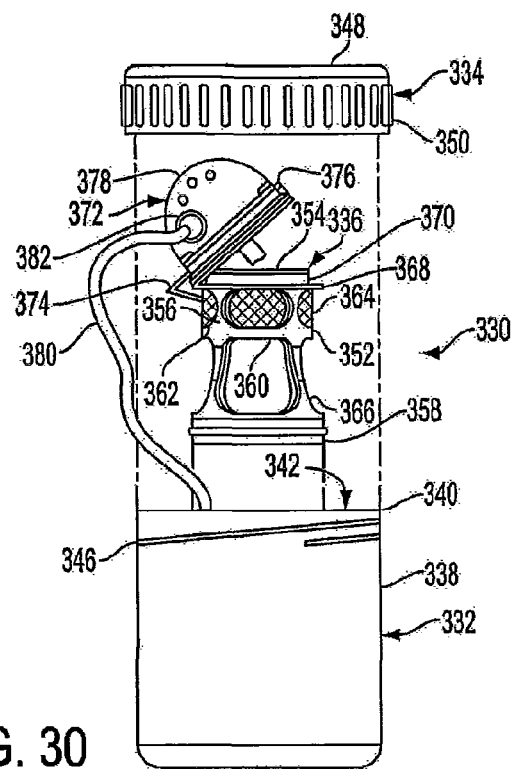
FIG. 30 is an exploded side view of the container in an embodiment where the sample holder is tethered to the container.
Figure 31:
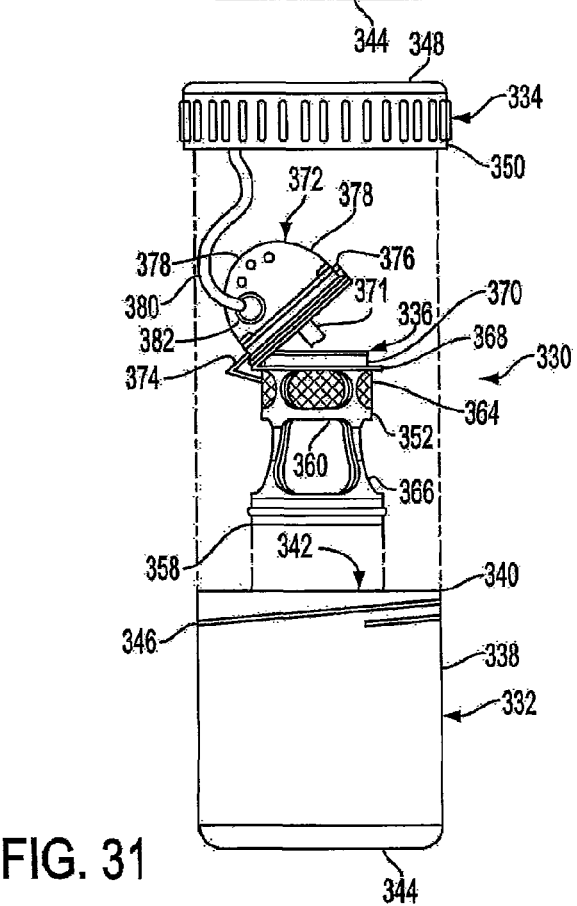
FIG. 31 is an exploded side view of the container in an embodiment where the sample holder is tethered to the cap of the container.

FIGS. 30 and 31 illustrate another embodiment of the invention. A container assembly 330 includes a container 332, a closure cap 334 and a sample holder 336.

Container 332 is similar to the containers of the previous embodiments and include a cylindrical side wall 338 having an upper end 340 defining an open top 342 and a bottom wall 344. Upper end 340 includes threads 346 for coupling closure cap 334 to container 332. Cap 334 has a top wall 348 and a depending side wall 350. Side wall 350 includes internal threads to mate with threads 346 on container 332.

Sample holder 336 is dimensioned to fit in container 332 to hold a biological sample in the reagent contained in container 332. In one embodiment, sample holder 336 has a width and height to limit lateral and longitudinal movement in container 332.

Sample holder 336 has a body 352 having an internal cavity and an open top end 354. Body 352 includes a side wall 356 extending from the open top end to a base 358. As shown in FIGS. 30 and 31, base 358 is flared in a generally outward direction from side wall 356 to a substantially flat bottom.

As in the previous embodiments, the bottom wall of the sample holder 336 has a permeable material such as a porous mesh 360 to define a liquid permeable bottom.

Side wall 356 includes a plurality of spaced-apart openings 362 covered by a permeable material such as a porous mesh 364 to enable a reagent to flow through the cavity. Base 358 also includes a plurality of spaced-apart openings 366 to allow the flow of a liquid reagent through the mesh into the cavity.

Side wall 356 of body 352 includes a radially extending flange 368 spaced from open top end 354 to define an annular collar 370. Sample holder 336 includes a closure member such as a cap 372 for closing open top end 354 of the cavity. In a preferred embodiment, cap 372 is coupled to body 352 by flexible hinge 374. Preferably, cap 372 is integrally formed with body 352 by a suitable plastic molding process.

Cap 372 includes an annular side wall 376 having a bottom end with an outwardly extending radial flange. Side wall 376 has an inner dimension complementing the outer dimension of collar 370. A post 371 extends downwardly from cap 372 a distance sufficient to position the biological sample in the cavity of sample holder 336 to keep the biological sample submerged in the reagent.

A tab 378 forming a handle extends upwardly from the top surface of cap 372 in an axial direction with respect to sample holder 336. Tab 378 includes a top end defining a height of sample holder 330. Preferably, the height of sample holder 336 complements the height of the container so that when cap 372 is coupled to the container, sample holder 336 is permitted limited axial movement within the container so that the cavity is retained within a predetermined area in the container. In one embodiment, sample holder 336 can be removably coupled to a bottom wall of container 332 to maintain sample holder 336 in a fixed location while transporting the biological sample.

In the embodiment of FIGS. 30 and 31, sample holder 336 is tethered to container 332 as in FIG. 30 or to cap 334 as in FIG. 31. A string 380 or strip of flexible material has a first end connected to cap 334 or container 332 and a second end extending through a hole 382 in tab 378. In this embodiment, sample holder 336 is connected to a component of assembly 330 that supports a label or other identifying indicia for identifying a biological sample. In this manner, the sample holder is continuously tethered to an identifying marker on the cap or container. In another embodiment, the container or lid is provided with a writable surface so that the identification can be written or printed on the container or cap.

EMBODIMENTS OF FIGS. 32-37

Figure 32:
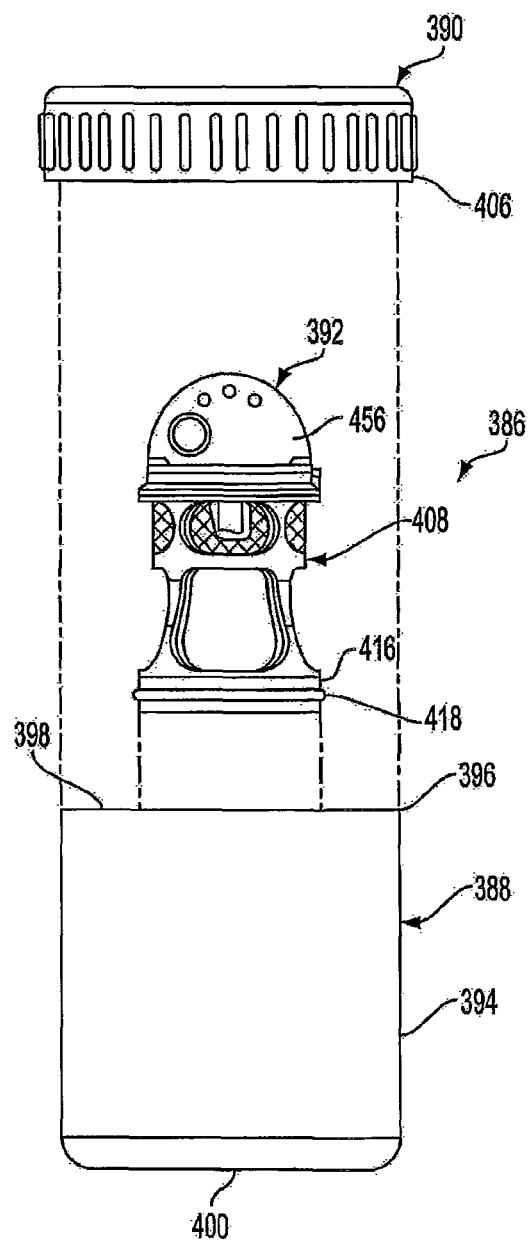
FIG. 32 is a side view of the container in a further embodiment of the invention.
Figure 37:
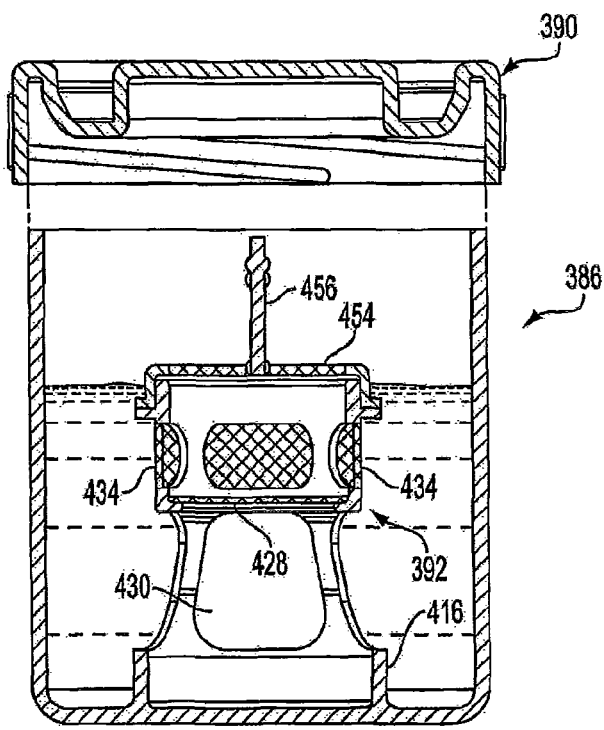
FIG. 37 is a cross-sectional view of the container assembly in another embodiment showing the sample holder fixed to the container.

Another embodiment of the invention is shown in FIGS. 32-37. Referring to FIG. 32, container assembly 386 includes a container 388, a closure cap 390 and a sample holder 392. In the embodiment of FIGS. 32-36, sample holder 392 is removably coupled to container 388 so that sample holder 392 remains in a fixed position within container 388. Sample holder 392 of FIGS. 32-36 is separable from container 388 for filing with a biological sample, after which sample holder 392 is returned and coupled to container 388. In the embodiment of FIG. 37, sample holder 392 is permanently fixed to container 388. Typically, sample holder 392 is integrally molded with container 388 in the embodiment of FIG. 37.

Container 388 has a cylindrical side wall 394 having an upper end 396 defining an open top end 398. A bottom wall 400 is coupled to a bottom end of side wall 394. Side wall 394 and bottom wall 400 define an internal cavity 402 for receiving sample holder 392. Upper end 396 of side wall 394 includes threads 402 on the outer face for mating with cap 390.

Figure 33:
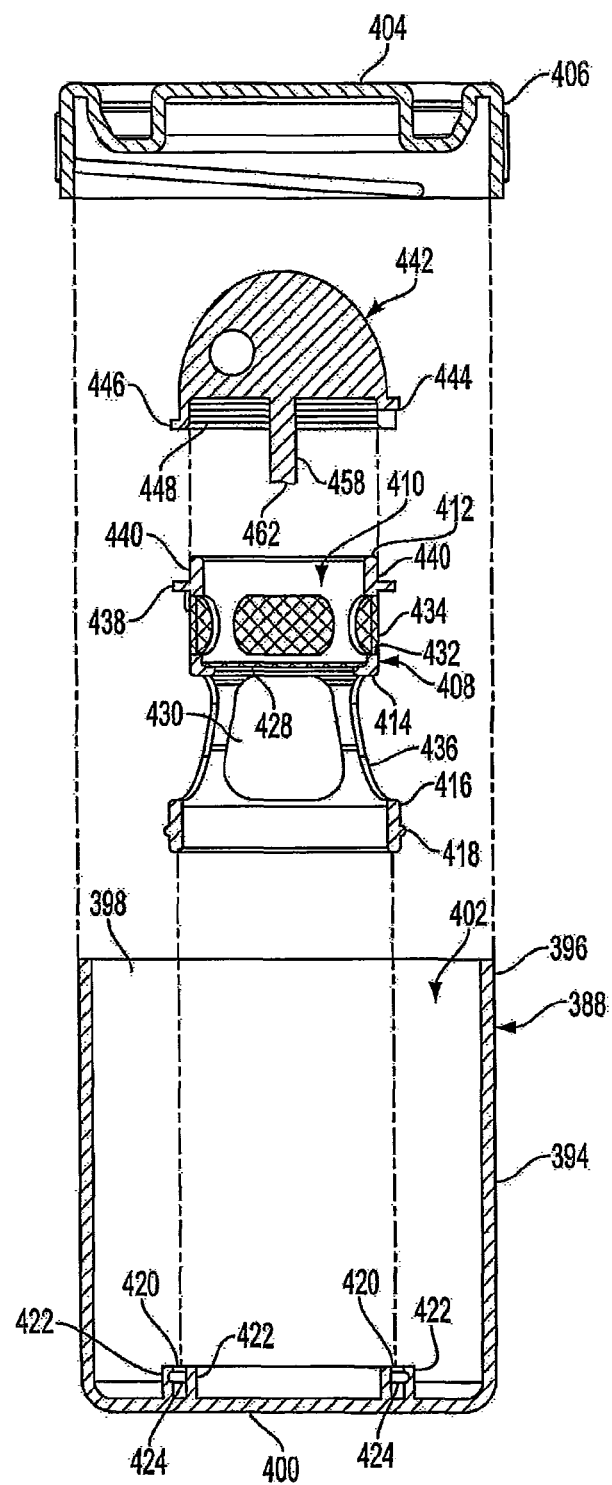
FIG. 33 is a cross-sectional side view of the container assembly of FIG. 32.

Cap 390 has a top wall 404 and a depending side wall 406. Side wall 406 includes threads on the inner face as shown in FIG. 33. Side wall 406 has a dimension to mate with upper end 396 of container 388.

Sample holder 392 is dimensioned to fit in container 398 and is easily removed from cavity 402. Sample holder 392 has a body 408 having an internal cavity 410 and an open top end 412. Body 408 includes a side wall 414 extending from open top end 412 to a base 416. As shown in FIG. 33, base 414 has a substantially cylindrical configuration with an outwardly extending radial rib 418. Bottom wall 400 of container 388 includes an annular recess 420 dimensioned to receive base 416 of sample holder 392 in a coupling relationship. In the embodiment illustrated, recess 420 is defined by concentric walls 422. The outermost wall 422 has an inwardly open groove 424 to receive rib 418 of base 414 to securely couple sample holder 392 to container 388. Sample holder 392 is removably coupled to container 398 by a press fit, such as an interference fit or friction fit.

In one preferred embodiment, sample holder 392 is securely attached to container 388 by a snap-fit between rib 418 and groove 424 to fix the location of sample holder 392 within container 388. Recess 420 formed by walls 422 define a coupling member for removably coupling sample holder 392 to container 388. Sample holder 392 is separable from container 388 by pulling upward with sufficient force to overcome the resistance between rib 418 and groove 424. In the embodiment shown in FIG. 37, sample holder 392 is integrally formed with container 388 and is not separable. Container 388 includes a writable surface for identification of the biological sample. Sample holder 392 can be separated from container 388 by pulling upward on sample holder 392 with respect to container 388.

Figure 34:
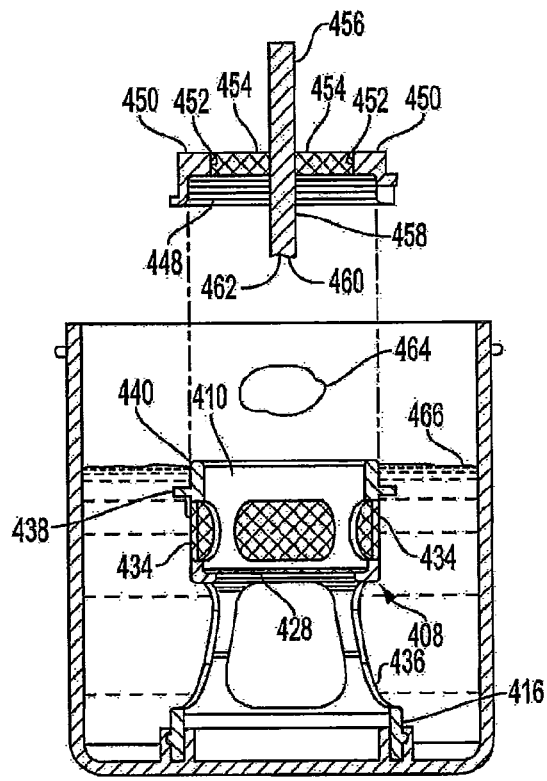
FIG. 34 is a cross-sectional side view of the container assembly of FIG. 32 showing the sample holder coupled to the container.
Figure 35:
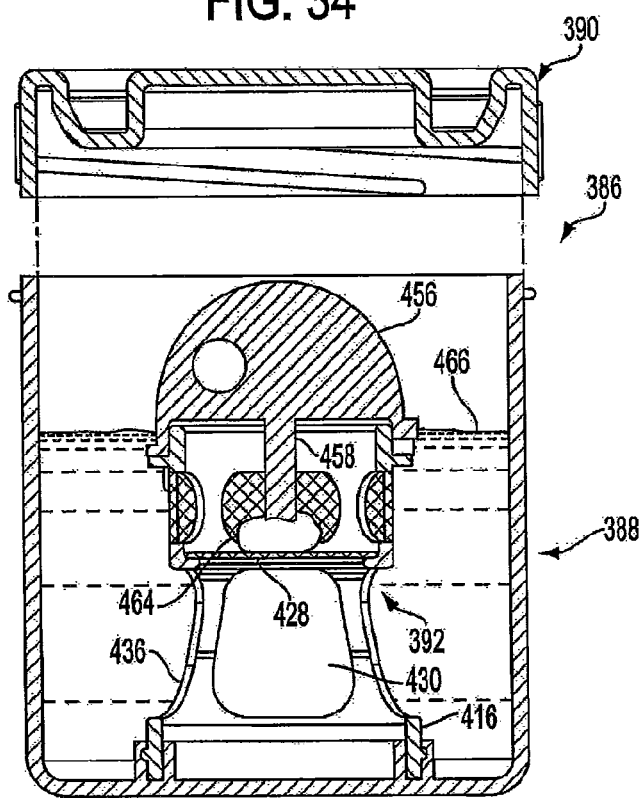
FIG. 35 is a cross-sectional side view showing the cap coupled to the sample holder in the container.
Figure 36:
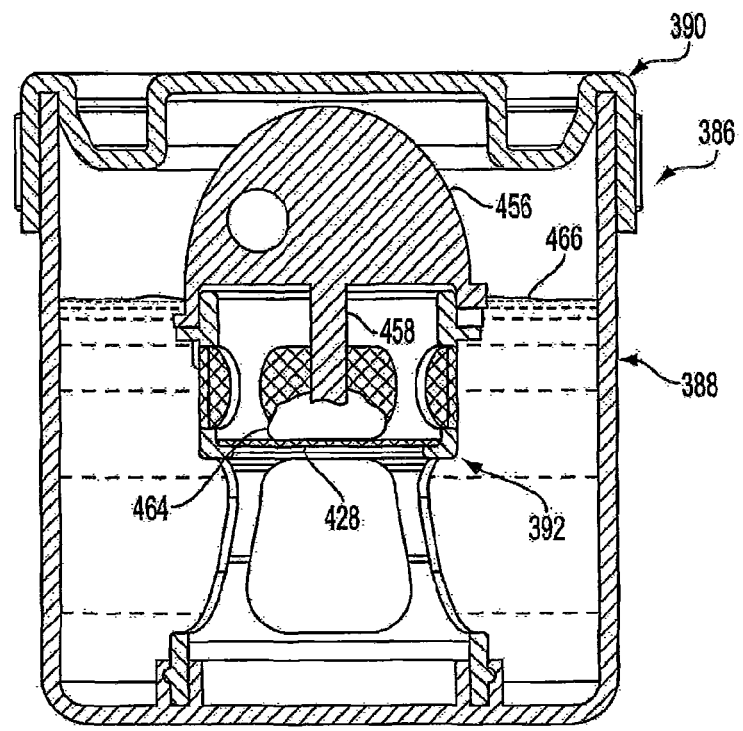
FIG. 36 is a cross-sectional side view of the container assembly containing a biological sample and a liquid reagent.

Referring to FIGS. 33 and 34, an internal ledge 426 extends radially inward from an inner surface of side wall 414. A permeable material such as a porous mesh 428 is coupled to ledge 426 to define a liquid permeable bottom of cavity 410. Ledge 426 and mesh 428 separate cavity 410 from a hollow portion 430 of base 416 and space cavity 402 from the bottom of container 388 when sample holder 392 is coupled to container 388 as shown in FIGS. 33 and 34.

Side wall 414 includes a plurality of spaced-apart openings 432 covered by a porous mesh 434 to enable a reagent to flow through cavity 402. Base 416 also includes a plurality of spaced-apart openings 436 to allow the flow of a liquid reagent into hollow portion 430 and through mesh 428 into cavity 402.

Side wall 414 of body 408 includes a radially extending flange 438 spaced from the open top end to define an annular collar 440. Sample holder 392 includes a closure member 442 in the form of a cap for closing the open top end of cavity 410. In the illustrated embodiment, cap 442 is separable from body 408 and is removably coupled to body 408 by a snap-fit.

Cap 442 includes an annular side wall 444 having a bottom end with an outwardly extending radial flange 446. Side wall 444 has an inner dimension complementing the outer dimension of collar 440. In the embodiment illustrated, side wall 444 includes a rib 448 on an inner surface for providing an interference fit of cap 442 with collar 440 of body 408.

Referring to FIG. 33, side wall 444 of cap 442 includes a top end with an inwardly extending radial flange 450. Flange 450 forms openings 452 which are covered by a permeable mesh 454. A tab 456 forming a handle extends upwardly from flange 450 in an axial direction with respect to sample holder 392. Tab 456 includes a top end defining a height of sample holder 392. Preferably, the height of sample holder 392 complements the height of container 388 so that when cap 442 is coupled to container 388, sample holder 392 is spaced closely to cap 390.

In one embodiment, container 388 is prefilled with a liquid reagent at the time of assembly and packaging of container assembly. When ready to be used by the technician or scientist, cap 390 is removed from container 388 and cap 442 is removed from body 408 of sample holder 392 to expose cavity 410. In one embodiment, container 388 is filled to a level to fill cavity 410 completely as shown in FIG. 34. Typically, the reagent level has a depth to immerse the biological sample in the reagent without the sample floating out of cavity 410. The biological sample is placed in cavity 410 and cap 390 is snapped onto body 408 of holder 392.

The biological sample can be placed in sample holder 392 while sample holder 392 remains coupled to container 388. Cap 442 of sample holder 392 can be removed from sample holder 392 without removing sample holder 392 from container 388. In this embodiment, the cavity of sample holder 392 is filled with the reagent. The biological sample is collected and placed directly into the reagent in the cavity of the sample holder 392 to minimize contamination and exposure of the biological sample to air. In alternative embodiments, sample holder 392 is separated from recess 420 and removed from container 388. Sample holder 392 can be placed in the inverted cap 390 to collect the reagent. The biological sample can be placed in the sample holder 392. Cap 442 is placed on sample holder 392. Sample holder 392 is then returned to the container 388 to immerse the biological sample in the reagent. Preferably, sample holder 392 is secured in the recess in container 388 to maintain sample holder 392 in a fixed location during shipping and handling of the assembly.

In the embodiment illustrated, cap 442 includes a post 458 extending downwardly from tab 456 into cavity 410 of sample holder 392 as shown in FIG. 34. Typically, post 458 is oriented to extend along the axis of cavity 410 and generally in the axial center of cavity 410. Post 458 has a substantially cylindrical shape with an axial end 460. Axial end 460 includes teeth 462 to engage the biological sample 464 and maintain the sample 464 immersed in the liquid reagent 466 in container 388. In one embodiment, post 458 has a width and length to capture biological sample 464 between axial end 460 of post 458 and bottom mesh 428 to fix the location of biological sample 464 during storage.

While various embodiments have been chosen to demonstrate the invention, it will be understood by those skilled in the art that various modifications and additions can be made without departing from the scope of the invention as defined in the appended claims.

What is claimed is:

1. A container assembly for storing a cell or biological sample, said assembly comprising:
   a container having a side, an open top end, a bottom, a stop member, and an internal dimension to contain a volume of a reagent sufficient to treat a biological sample;
   a cap for coupling to and closing said open top end of said container; and
   a sample holder detached from said cap, having an internal cavity with a bottom and a dimension for receiving a biological sample, said sample holder having a plurality of fluid openings into said cavity to enable free flow of said reagent into said cavity, said sample holder having a dimension to fit in said container below said cap and to immerse said cavity in said reagent,
   wherein said sample holder is supported in said container by contact with said stop member wherein said stop member comprises at least one protrusion extending from at least a portion of said side of said container, and
   wherein said bottom of said cavity is spaced from said bottom of said container.

2. A container assembly for storing a cell or biological sample, said assembly comprising:
   a reagent;
   a container having a side, an open top end, and an internal dimension to contain a volume of said reagent sufficient to treat a biological sample;
   a cap for coupling to and closing said open top end of said container; and
   a sample holder detached from said cap, having a closure member and an internal cavity with a dimension for receiving a biological sample, said sample holder having a plurality of fluid openings into said cavity to enable free flow of said reagent into said cavity, said sample holder having a dimension to fit in said container below said cap and to immerse said cavity in said reagent
   wherein the sample holder is detached from said cap when said cap is engaged with the open top end of said container.

3. The container assembly of claim 2, wherein said closure member cooperates with said cap to ensure said internal cavity of said sample holder remains immersed in said reagent.

4. The container assembly of claim 2, said reagent further comprising a stabilizing agent.

5. The container assembly of claim 2, said reagent further comprising a nucleic acid stabilizing agent.

6. The container assembly of claim 2, said reagent further comprising a lysing agent.

7. The container assembly of claim 2, said reagent further comprising a drying agent.

8. The container assembly of claim 2, said reagent further comprising a preservation reagent.

9. The container assembly of claim 2, said reagent further comprising a cationic detergent.

* * * * *